(12) United States Patent
Friese et al.

(10) Patent No.: US 7,445,933 B2
(45) Date of Patent: *Nov. 4, 2008

(54) STABLE CALIBRATORS OR CONTROLS FOR MEASURING HUMAN NATRIURETIC PEPTIDES

(75) Inventors: Judith A. Friese, Hinsdale, IL (US); Matthew S. Matias, Libertyville, IL (US); Ray A. Weigand, Wadsworth, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 322 days.

This patent is subject to a terminal disclaimer.

(21) Appl. No.: 10/620,475

(22) Filed: Jul. 16, 2003

(65) Prior Publication Data

US 2005/0014287 A1    Jan. 20, 2005

(51) Int. Cl.
    *G01N 31/00*    (2006.01)
(52) U.S. Cl. .............. 436/15; 435/967; 436/8
(58) Field of Classification Search .......... 435/71.1, 435/4, 23, 188; 514/21, 12, 14; 530/300, 530/350; 436/8, 15, 18
    See application file for complete search history.

(56) References Cited

U.S. PATENT DOCUMENTS

| | | | | |
|---|---|---|---|---|
| 5,352,587 A * | 10/1994 | Chang et al. | ............ | 514/12 |
| 5,358,691 A | 10/1994 | Clark et al. | ............ | 422/64 |
| 5,541,116 A | 7/1996 | Bergmann et al. | ........ | 436/176 |
| 6,376,207 B1 | 4/2002 | Mischak et al. | ............ | 435/7.94 |
| 6,407,211 B1 * | 6/2002 | Burnett et al. | ............ | 530/350 |
| 6,525,102 B1 * | 2/2003 | Chen et al. | ............ | 424/85.2 |
| 2005/0136542 A1 * | 6/2005 | Todtleben et al. | ........ | 436/15 |

FOREIGN PATENT DOCUMENTS

| EP | 1030177 A1 | 8/2000 |
|---|---|---|
| EP | 1378242 A1 | 1/2004 |
| JP | 05170664 | 10/1993 |
| WO | WO 96/27661 | * 9/1996 |

OTHER PUBLICATIONS

Motwani, et al., "Plasma brain natriuretic peptide as an indicator for angiotensin-converting-enzyme inhibition after myocardial infraction". The Lancet, 341:1109-1113, (1997).

Cataliotti, et al., "Circulating Natriuretic Peptide Concentrations in Patients With End-Stage Renal Disease: Role of Brain Natriuretic Peptide as a Biomaker for Ventricular Remodeling". Mayo Foundation for Medical Education and Research, 76:1111-1119, (2001).

Mukoyama, et al., "Brain Natriuetic Peptide as a Novel Cardiac Hormone in Humans." Journal Clinical Investigation, 87:11402-11412, (1991).

Yandle, T.G., "MINISYMPOSIUM: The Natriuretic Peptide Hormones; Biochemistry of natriuretic peptides", Journal of Internal Medicine. 235:561-576, (1994).

Murdoch, et al., "Brain natriuretic peptide is stable in whole blood and can be measured using a simple rapid assay: implications for clinical practice". Heart 1997; 78:594-597.

Davidson et al., "Brain natriuretic peptide". Journal of Hypertension, 1994; 12:329-336.

Yoshibayashi, et al., "Increased Plasma Levels of Brain Natriuretic Peptide in Hypertrophic Cardiomyopathy". The New England Journal of Medicine, 1993; vol. 32, No. 6, pp. 433-435.

Shimizu, et al., "Molecular forms of human brain natriuretic peptide in plasma". Clinica Chimica Acta, 2002; 129-135.

Tsuji Tetsuo et al., *Clinical Chemistry* "Stabilization of human brain natriuretic peptide in blood samples" 40(4):672-673 (1994).

Gutkowskaj et al., *Biochemical and Biophysical Research Comm* "Atrial natriuretic factor in human plasma" 139(1):287-295 (Aug. 1986).

Kelly P M et al., *Clinical Chemistry* "A novel assay for the measurement of plasma B-type natriuretic peptide by an AxSYN® microparticle based immunoassay with use of stable liquid calibrators" 48(6):A94 (Jun. 2002).

\* cited by examiner

*Primary Examiner*—Ralph Gitomer
(74) *Attorney, Agent, or Firm*—Audrey L. Bartnicki

(57) ABSTRACT

The present invention relates to a stable liquid calibrator or control for use in ligand-binding assays wherein the calibrator or control comprises at least one human synthetic natriuretic peptide and has a pH of from about 4.0 to about 6.5 and remains stable when stored at temperatures of from about 2 to about 8°C. for a period of about twelve months.

35 Claims, 19 Drawing Sheets

STABLE CALIBRATORS OR CONTROLS FOR MEASURING HUMAN NATRIURETIC PEPTIDES

FIELD OF THE INVENTION

The present invention relates to stable calibrators and controls that can be used in ligand-binding assays, such as immunoassays, and methods for making said calibrators and controls.

BACKGROUND OF THE INVENTION

Atrial natriuretic peptide (hereinafter referred to as "ANP"), brain natriuretic peptide (hereinafter referred to as "BNP"), C-type natriuretic peptide (hereinafter referred to as "CNP") and Dendroaspis natriuretic peptide (hereinafter referred to as "DNP") are each members of a family of hormones known as "natriuretic peptides". ANP and BNP share a wide spectrum of biological properties and belong to the cardiac natriuretic system. Both ANP and BNP are of myocardial cell origin while CNP is of endothelial cell origin. DNP was isolated from the venom of the green mamba snake and possesses structural similarity to ANP, BNP and CNP.

BNP received its name because it was first isolated from porcine brain, thus "BNP" stood for "brain natriuretic peptide". However, because BNP belongs to the cardiac natriuretic system, "brain" has been changed to "B-type". Therefore, "BNP" now refers to "B-type natriuretic peptide".

ANP is secreted by the heart in the atria. BNP is secreted by the heart through the coronary sinus, predominantly from the cardiac ventricles. BNP is secreted as a 108 amino acid polypeptide precursor (See Valli et al., *J. Lab. Clin. Med.*, 134(5):437–444 (November 1999)). The mature form of BNP is made up of 32 amino acids with a 17 amino acid ring closed by a disulfide bond between two cysteine residues, an amino-terminal tail of 9 amino acids, and a carboxyl-terminal tail of 6 amino acids. ANP and CNP also have a 17 amino acid ring closed by a disulfide bond between two cysteine residues. Eleven of the seventeen amino acids in the ring are conserved between the three molecules. In addition to the 17 amino acid ring structure, ANP has an amino-terminal tail of 6 amino acids and a carboxy-terminal tail of 5 amino acids. ANP is produced as a 126 amino acid pro-ANP form that is the major storage form of ANP. After proteolytic cleavage between amino acids 98 and 99, the mature 28 amino acid peptide ANP is found in coronary sinus plasma (See Yandle, *J. Internal Med.*, 235:561–576 (1994)).

CNP is found in the brain and cerebral spinal fluid and is the most prevalent of the three peptides in the central nervous system. Little if any CNP is present in the heart. Pro-CNP is a 103 amino acid peptide that is processed into either CNP-53 (amino acids 51 to 103) or CNP-22 (amino acids 82 to 103) that are the active peptides. In addition the 17 amino acid ring structure, CNP-22 has an amino-terminal tail of 5 amino acids and contains no carboxy-terminal tail. CNP-53 is identical to CNP-22 except for a 31 amino acid extension at the amino terminal end.

As mentioned previously, DNP was isolated from the venom of the green mamba snake. The mature form of DNP is made up of 38 amino acids. DNP-like immunoreactivity (DNP-LI) has been reported in human plasma and the plasma concentration of DNP-LI has been found to be elevated in patients with congestive heart failure (See, Cataliotti, et al., *Mayo Clin. Proc.*, 76:111–1119 (2001)). Additionally, it is also known that the infusion of synthetic DNP results in marked natriuresis and diuresis in association with increased plasma and urinary cyclic guanosine monophosphate. Id.

The measurement of BNP in human plasma in the general population has been found to reflect cardiac diseases, such as congestive heart failure, ischemic heart diseases, atrial fibrillation and renal dysfunction. In fact, elevated levels of BNP in human plasma has been reported in heart disease, following acute myocardial infarction and during symptomless or subclinical ventricular dysfunction (See Mukoyama et al., *J. Clin. Invest.*, 87:11402–11412 (1991), Motwani et al., *Lancet*, 341:1109–1113 (1993), Yoshibayashi et al., *New Eng. J. Med.*, 327:434 (1992)). Increased circulating levels of ANP are seen in congestive heart failure, chronic renal failure and in severe hypertension. The presence of CNP in human plasma remains controversial with reports of its absence or presence as CNP-22 (See Yandle, *J. Internal Med.*, 235:561–576 (1994)).

A ligand binding assay is an analytical technique for measuring concentrations of substances commonly referred to as ligands that react selectively with specific binding proteins. Immunoassays that measure the concentrations of antigens that react selectively with specific antibodies are an example of a class of ligand binding assays.

Ligand binding assays, such as immunoassays, for measuring human natriuretic peptides in plasma are well-known in the art and are commercially available. These immunoassays require the use of at least one or two specific antibodies as well as at least one calibrator and, ideally, at least one control. Calibrators are used in ligand binding assays to calibrate instruments prior to calculating the sample result. The calibrators and controls used in such assays are typically made from human synthetic natriuretic peptides. Human synthetic natriuretic peptides are commercially available from a variety of sources. For example, human synthetic BNP is commercially available from Peptide Institute (Osaka, Japan), American Peptide Company, Inc. (Sunnyvale, Calif.), Synpep Corporation (Dublin, Calif.) and Phoenix Pharmaceuticals, Inc. (Belmont, Calif.).

One of the problems with both natural and synthetic human natriuretic peptides is that they are unstable in plasma and serum. Specifically, enzymes, such as proteases, cleave these peptides. For example, proteases cleave BNP (natural and synthetic) at various locations along its amino acid chain. For example, protease cleavage is known to occur at the amino terminus of BNP between amino acids 2–3 (Shimizu et al., *Clinica Chimica Acta*, 316:129–135 (2002)) and at its carboxy terminus between amino acids 30–32. Moreover, endopeptidase cleavage of BNP is also known in the art (Davidson and Struthers, *J. Hypertension*, 12:329–336 (1994)). Such cleavage is problematic because in order for calibrators and controls to function properly in an assay, a human natriuretic peptide containing immunoreactive or specific ligand binding sites must be present at the intended concentration during the assay.

Thereupon, as a result of this instability, the calibrators and controls used in such assays are sold either in lyophilized form (such as in the Shionoria assay available from Shionogi & Co., Ltd., Osaka, Japan) or frozen (such as in the Triage® assay available from Biosite, Inc., San Diego, Calif.). Calibrators and controls in lyophilized form must be reconstituted in a solvent prior to use in an assay. Once reconstituted, these calibrators and controls must be used within a specific time because they are very unstable. Calibrators and controls that are frozen (usually at temperatures of about −20° C. or colder) remain frozen until thawed for use in the assay. These calibrators and controls are thawed at room temperature and then vortexed or inverted to make the calibrators and controls homogenous prior to testing. Frozen calibrators and controls cannot be re-frozen and can only be used once (i.e. are single-use) and then discarded.

Thereupon, there is a need in the art for new calibrators and controls for use in human natriuretic ligand binding assays that are stable for extended periods of time and are easy and quick to use and do not need to be reconstituted or thawed prior to use in such assays.

SUMMARY OF THE INVENTION

In one embodiment, the present invention relates to stable liquid calibrators and controls that can be used in ligand binding assays, such as immunoassays, for measuring the level of natriuretic peptides in a test sample. The stable liquid calibrators and controls of the present invention have a pH of from about 4.0 to about 6.5, preferably from about 5.0 to about 6.0.

Moreover, the calibrators and controls of the present invention comprise at least one natriuretic peptide, preferably at least one human synthetic natriuretic peptide, such as a human synthetic atrial natriuretic peptide, human synthetic B-type natriuretic peptide, human synthetic C-type natriuretic peptide or human synthetic Dendroaspis natriuretic peptide. In addition to the natriuretic peptide, the calibrators and controls can also comprise at least one buffer, at least one acid, at least one base, or combinations thereof. Examples of buffers that can be used include, but are not limited to, acetate buffers (such as sodium acetate/acetic acid, potassium acetate/acetic acid), citrate buffers (such as sodium citrate/citric acid, potassium citrate/citric acid), phosphate buffers (such as mono-/di-sodium phosphate) or combinations thereof. Examples of acids that can be used include, but are not limited to, acetic acid, citric acid, diethylenetriaminepentaacetic acid, hydrochloric acid or combinations thereof. Examples of bases that can be used include, but are not limited to, sodium hydroxide.

The calibrators and controls can also comprise at least one diluent. The diluent can comprise at least one natriuretic stabilizing compound and at least one biocide. Examples of natriuretic stabilizing compounds that can be used include, but are not limited to, at least one protein or polymer. Examples of proteins that can be used include, but are not limited to, bovine serum albumin, bovine gamma globulin, or non-fat dry milk. Examples of polymers that can be used include, but are not limited to, polyethylene glycol, dextran, dextran sulfate or polyvinyl pyrrolidone. The diluent can further contain at least one buffer, at least one acid, at least one base, or combinations thereof. Examples of buffers that can be used include, but are not limited to, acetate buffers (such as sodium acetate/acetic acid, potassium acetate/acetic acid), citrate buffers (such as sodium citrate/citric acid, potassium citrate/citric acid), phosphate buffers (such as mono-/di-sodium phosphate) or combinations thereof. Examples of acids that can be used include, but are not limited to, acetic acid, citric acid, diethylenetriaminepentaacetic acid, hydrochloric acid or combinations thereof. Examples of bases that can be used include, but are not limited to, sodium hydroxide.

The calibrators and controls of the present invention remain stable for long periods of time under a variety of storage conditions. Specifically, the calibrators and controls of the present invention remain stable when stored for extended periods of time at a temperature of from about 2 to about 8° C. Additionally, the calibrators and controls of the present invention remain stable when used at ambient temperatures and for limited periods of time (such as between 1 minute and 60 minutes, preferably for a period of about 20 to about 30 minutes) at temperatures of from about 30 to about 40° C., preferably at a temperature of about 34° C.

In a second embodiment, the present invention relates to a method of making stable liquid calibrators and controls for use in a ligand binding assay. The first step of the method involves mixing at least one diluent with at least one human synthetic natriuretic peptide to form a liquid calibrator or control. The second step involves measuring the pH of the liquid calibrator or control. Depending upon the pH of the liquid calibrator or control measured in the first step, the pH of the liquid calibrator or control may be adjusted so that the pH is in the range of from about 4.0 to about 6.5, preferably in the range from about 5.0 to about 6.0. The pH of the calibrator or control can be adjusted using at least one buffer, at least one acid, at least one base or combinations thereof. Examples of buffers that can be used include, but are not limited to, acetate buffers (such as sodium acetate/acetic acid, potassium acetate/acetic acid), citrate buffers (such as sodium citrate/citric acid, potassium citrate/citric acid), phosphate buffers (such as mono-/di-sodium phosphate) or combinations thereof. Examples of acids that can be used include, but are not limited to, acetic acid, citric acid, diethylenetriaminepentaacetic acid, hydrochloric acid or combinations thereof. An example of a base that can be used is sodium hydroxide.

The human synthetic natriuretic peptide used in the above-described method can be human synthetic atrial natriuretic peptide, human synthetic B-type natriuretic peptide, human synthetic C-type natriuretic peptide or human synthetic Dendroaspis natriuretic peptide.

The diluent used in above described method can comprise at least one natriuretic stabilizing compound and at least one biocide. Examples of natriuretic stabilizing compounds, include, but are not limited to, at least one protein or polymer. Examples of proteins that can be used include, but are not limited to, bovine serum albumin, bovine gamma globulin or non-fat dry milk. Examples of polymers that can be used include, but are not limited to, polyethylene glycol, dextran, dextran sulfate or polyvinyl pyrrolidone. The diluent can further contain at least one buffer, at least one acid, at least one base, or combinations thereof. Examples of buffers that can be used include, but are not limited to, acetate buffers (such as sodium acetate/acetic acid, potassium acetate/acetic acid), citrate buffers (such as sodium citrate/citric acid, potassium citrate/citric acid), phosphate buffers (such as mono-/di-sodium phosphate) or combinations thereof. Examples of acids that can be used include, but are not limited to, acetic acid, citric acid, diethylenetriaminepentaacetic acid, hydrochloric acid or combinations thereof. Examples of bases that can be used include, but are not limited to, sodium hydroxide.

DETAILED DESCRIPTION OF THE INVENTION

Figure 1A:
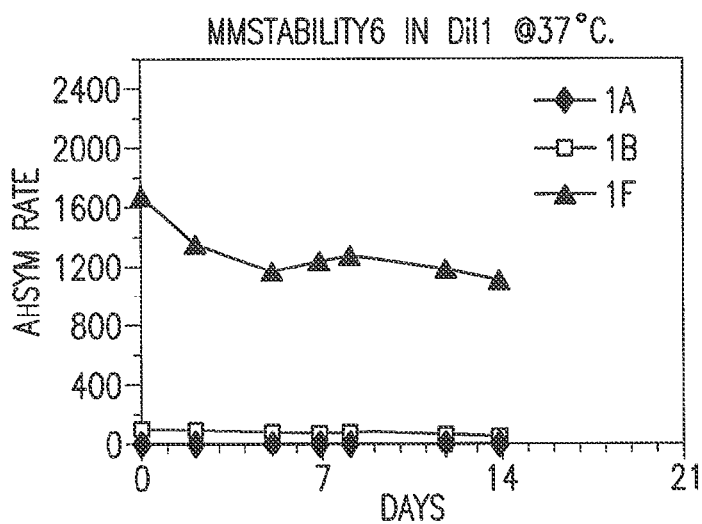
FIGS. 1A-1P shows graphs demonstrating the stability of calibrators having varying pH's at 37° C. over time.
Figure 1B:
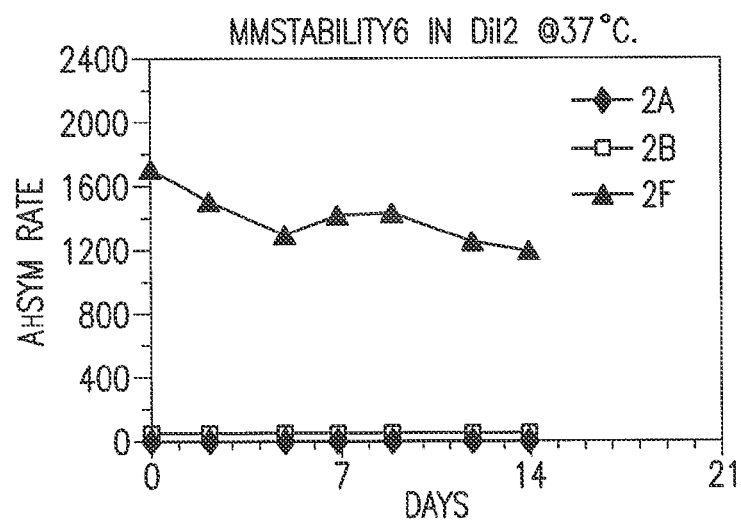
Figure 1C:
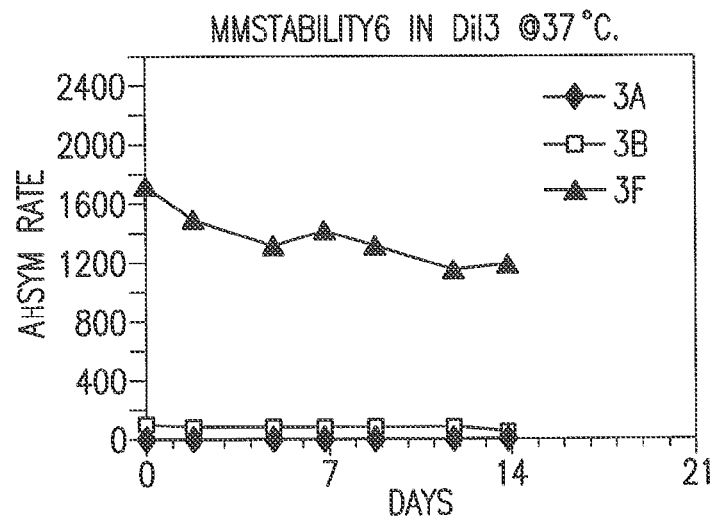
Figure 1D:
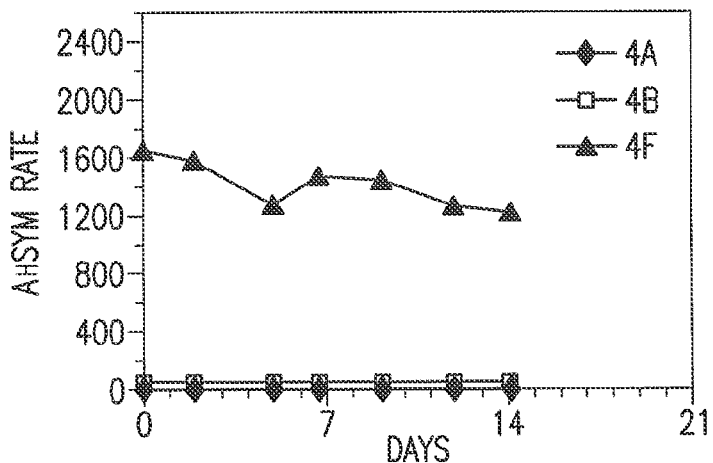
Figure 1E:
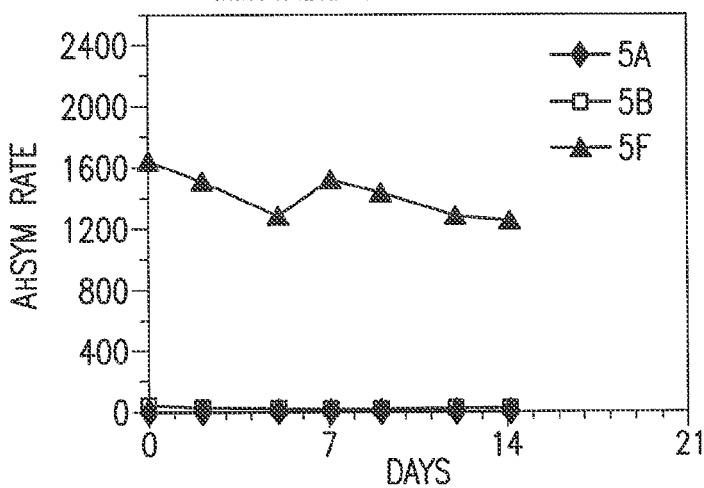
Figure 1F:
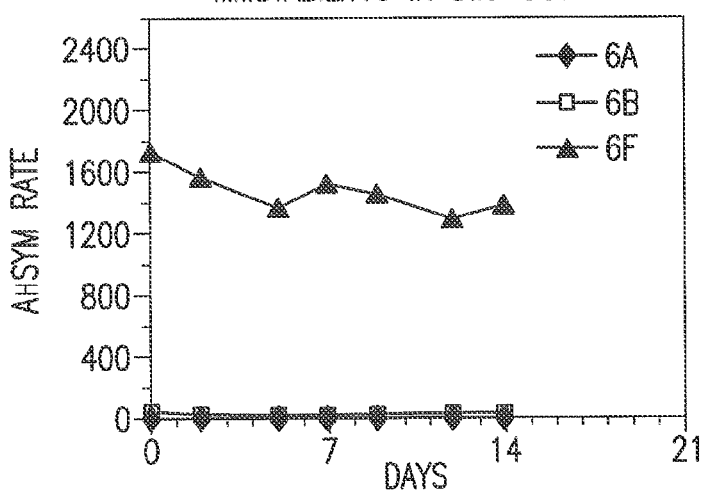
Figure 1G:
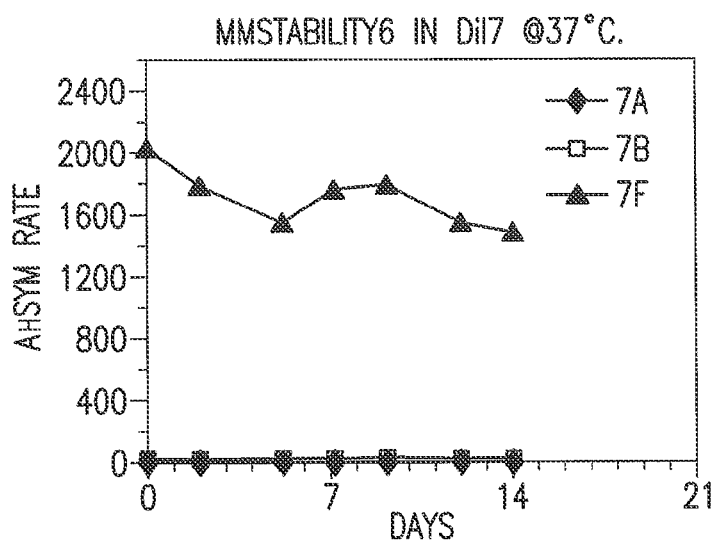
Figure 1H:
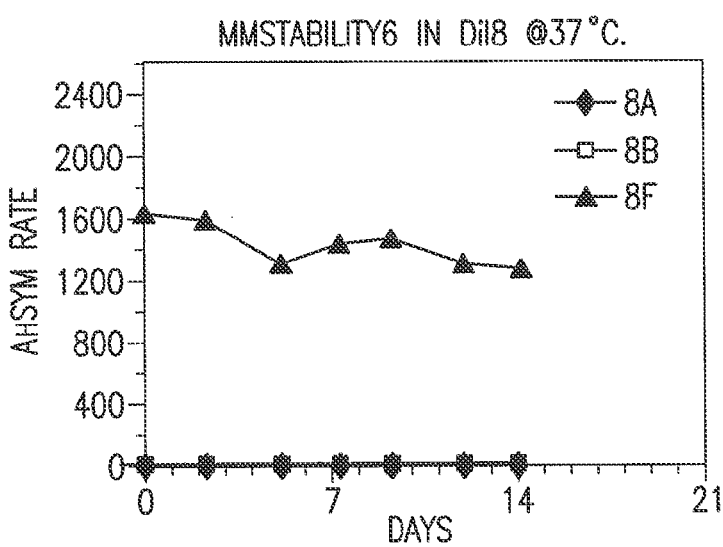
Figure 1I:
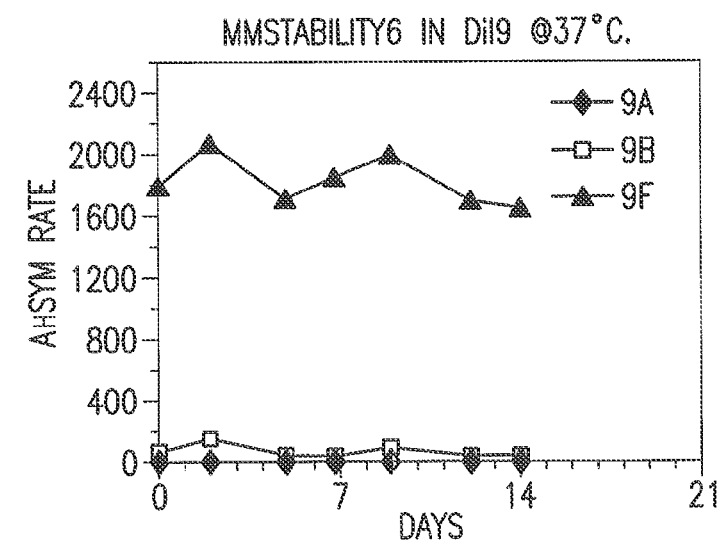
Figure 1J:
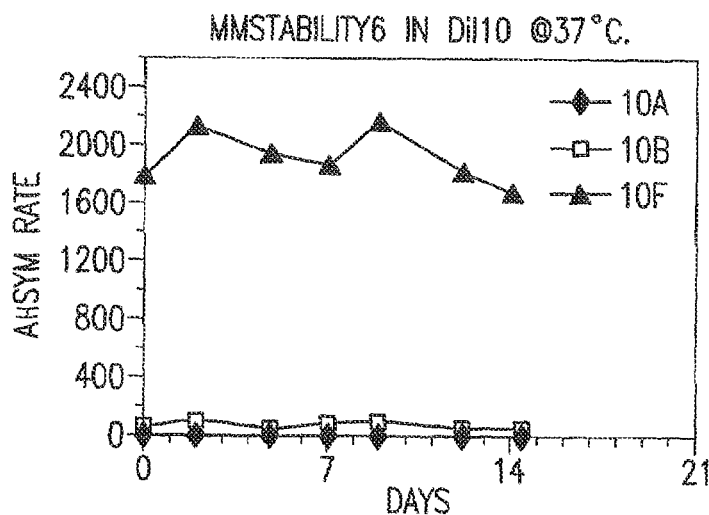
Figure 1K:
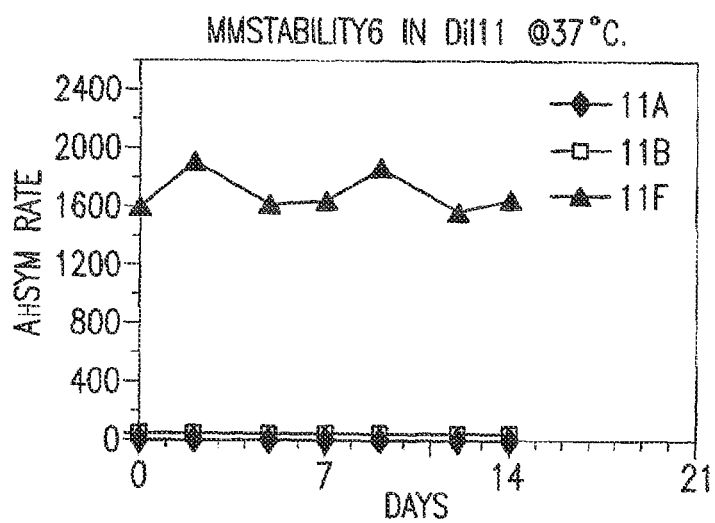
Figure 1L:
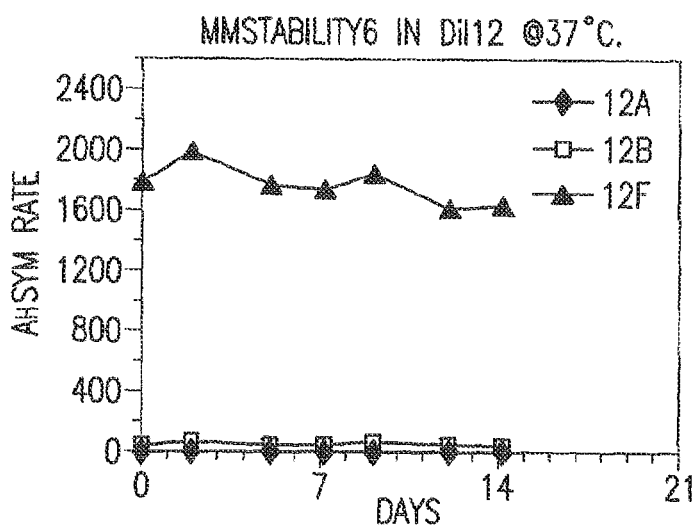
Figure 1M:
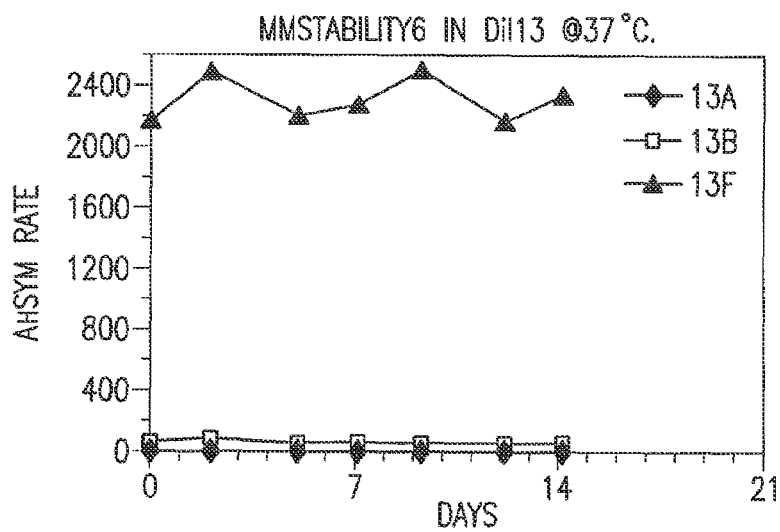
Figure 1N:
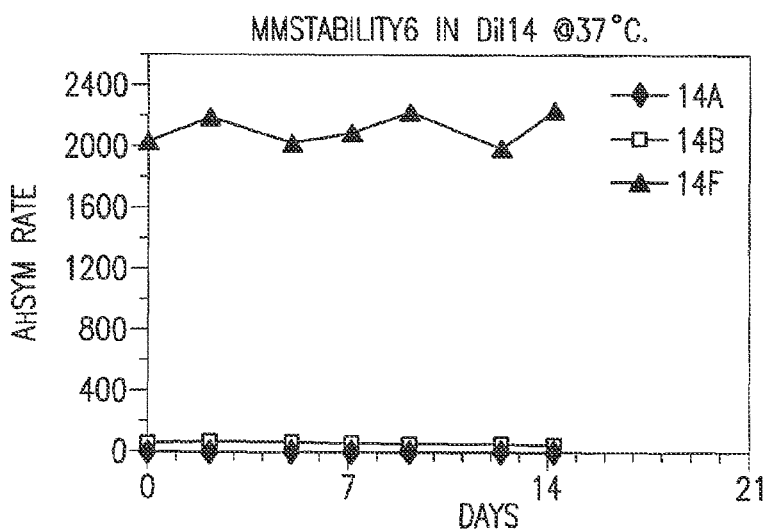
Figure 1O:
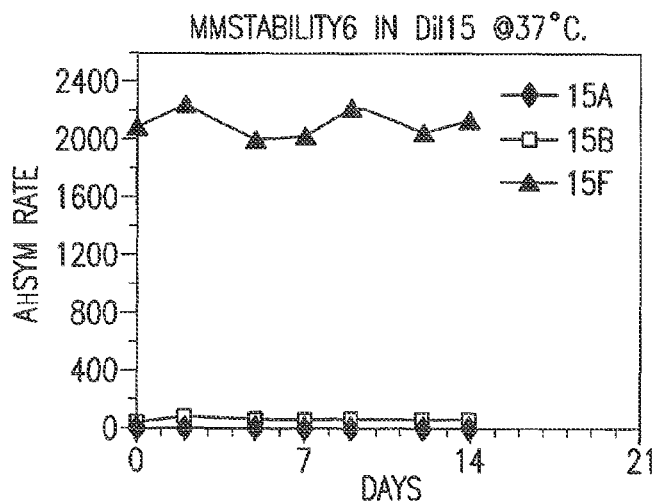

In one embodiment, the present invention relates to stable calibrators and controls that can be used in ligand binding assays, such as immunoassays. More specifically, the present invention relates to stable calibrators and controls that are in liquid form and can be used in ligand binding assays to measure the levels of at least one natriuretic peptide in a test sample. The test sample can be derived from human plasma, human serum, whole blood or other bodily fluids, such as, but not limited to, saliva, sputum, etc., as long as the bodily fluids are stable in their collection technique. Because the calibrators and controls of the present invention are in liquid form, they do not need to be reconstituted or defrosted prior to use like the lyophilized and frozen calibrators and controls known in the art. Additionally, the calibrators and controls of the present invention are stable for long periods of time under a variety of storage conditions and temperatures.

The calibrators and controls of the present invention contain at least one natriuretic peptide and thus can be used in ligand binding assays to measure the level of these peptides in a test sample. Either natural or synthetic natriuretic peptides can be used in the calibrators and controls of the present invention. Preferably, the natriuretic peptides are synthetic natriuretic peptides and are human, such as, human synthetic atrial natriuretic peptide, human synthetic B-type natriuretic peptide, human synthetic C-type natriuretic peptide or human synthetic Dendroaspis natriuretic peptide. Human synthetic atrial natriuretic peptides, human synthetic B-type natriuretic peptides, human synthetic C-type natriuretic peptides and human synthetic Dendroaspis natriuretic peptides are commercially available from a variety of sources, including, but not limited to, Peptide Institute (Osaka, Japan), American Peptide Company, Inc. (Sunnyvale, Calif.), Synpep Corporation (Dublin, Calif.) and Phoenix Pharmaceuticals, Inc. (Belmont, Calif.). The amount of natriuretic peptides in the calibrators of the present invention is from 0 to about 10,000 pg/mL, preferably in the amount of from about 25 to about 5,000 pg/mL. The amount of natriuretic peptides in the controls of the present invention is from about 25 to about 4000 pg/mL, preferably in the amount of from about 40 to about 2000 pg/mL.

In addition to the natriuretic peptides, the calibrators and controls are in a diluent that comprises a number of components. Any diluent can be used in the calibrators and controls of the present invention. For example, a diluent that can be used in the calibrators and controls of the present invention can be made using techniques known in the art or can be a purchased from a commercially available source. Combinations of both custom made diluents and commercially purchased diluents are also contemplated within the scope of the present invention.

The composition of the diluent can vary depending upon the calibrator or control. For example, the diluent can comprise water.

The diluent can also comprise at least one natriuretic stabilizing compound. As used herein, the term "natriuretic stabilizing compound" refers to a compound that can be used to stabilize a natriuretic peptide and prevent its degradation by enzymes, such as proteases. Several natriuretic stabilizing compounds are known in the art and can be used in the calibrators and controls of the present invention. These compounds include, but are not limited to, proteins, polymers and protease inhibitors. Examples of proteins that can be used include, but are not limited to, bovine serum albumin (BSA), bovine gamma globulin (bovine IgG), or non-fat dry milk (such as Nestlé® Carnation® Nonfat Dry Milk). Examples of polymers that can be used include, polyethylene glycol (having a molecular weight of from about 2,000 to about 20,000 daltons), dextran (having a molecular weight of from about 5,000 to about 670,000 daltons), dextran sulfate (having a molecular weight of about 5,000 daltons or about 1,000,000 daltons) or polyvinyl pyrrolidone (having a molecular weight of about 40,000 daltons). Bovine serum albumin, bovine IgG, polyethylene glycol, dextran, dextran sulfate and polyvinyl pyrrolidone can all be purchased from Sigma Aldrich, St. Louis, Mo. Examples of protease inhibitors that can be used include, but are not limited to, EDTA or aprotinin. It is known in the art that EDTA at about 1 mg/mL blood and aprotinin at approximately 50 kIU/mL of blood (Murdoch et al, *Heart*, 78:594–597 (1997)) can be used to help prevent BNP proteolysis. Protease inhibitors, such as EDTA and aprotinin can be purchased from Sigma Aldrich, St. Louis, Mo. The amount of natriuretic stabilizing compound in the diluent can be from about 0.01 mg/mL to about 400 mg/mL, preferably in the amount of from about 1 mg/mL to about 50 mg/mL.

Additionally, the diluent can also comprise and at least one biocide and/or preservative. As used herein, the term "biocide" refers to a substance that can be used to kill a variety of different organisms. Suitable biocides and/or preservatives for use in the diluent can be determined using routine techniques by those skilled in the art. Examples of suitable biocides and/or preservatives that can be used in the present invention, include, but are not limited to ProClin® 300 (Sigma-Aldrich, St. Louis, Mo.) (The active ingredients of ProClin® 300 are 5-chloro-2-methyl-4-isothiazolin-3-one and 2-methyl-4-isothiazolin-3-one and sodium azide. ProClin® 300 also contains a number of inert ingredients such as a modified glycol and alkyl carboxylate.). The amount of biocide and/or preservative in the diluent can be from about 0.001 mg/mL to about 50 mg/mL, preferably in the amount of from about 0.1 mg/mL to about 10 mg/mL.

Furthermore, the diluent can also comprise at least one buffer, at least one acid, at least one base or combinations thereof. Examples of buffers that can be used include, but are not limited to, acetate buffers (such as sodium acetate/acetic acid, potassium acetate/acetic acid), citrate buffers (such as sodium citrate/citric acid, potassium citrate/citric acid), phosphate buffers (such as mono-/di-sodium phosphate) or combinations thereof. It is preferred that the buffer have a good buffering capacity at the desired pH so that it can stabilize the pH of the diluent and the resulting calibrator or control. Examples of acids that can be used include, but are not limited to, acetic acid, diethylenetriaminepentaacetic acid (DTPA), hydrochloric acid (HCl) or combinations thereof. The amount of buffer or acid in the diluent can be from about 1 mM to about 500 mM, preferably in the amount of from about 5 to about 200 mM. An example of a base that can be used includes, but is not limited to, sodium hydroxide (NaOH). The amount of base in the diluent can be from about 0.01 mM to about 50 mM, preferably in the amount of from about 1.0 mM to about 10 mM.

The diluent can also comprise sodium chloride (NaCl) and/or at least one detergent, such as Tween® (Any type of Tween® can be used, including, but not limited to, Tween® 20, Tween® 40, Tween® 60, which are commercially available from Sigma-Aldrich, St. Louis, Mo.). The amount of NaCl in the diluent can be from about 25 mM to about 500 mM, preferably in the amount of from about 100 mM to about 400 mM. The amount of detergent in the diluent can be from about 0.01 mg/mL to about 10 mg/mL, preferably in the amount of from about 0.1 mg/mL to about 3.0 mg/mL.

In addition, as mentioned above, commercially available diluents can be used. For example, the diluent known as "MEIA2" that is commercially available as IMx MEIA #2 Diluent Buffer (No.8374-04) from Abbott Laboratories, the assignee of the present invention, can be used. MEIA2 contains 0.06 M Tris buffer (Sigma-Aldrich, St. Louis, Mo.), 0.3 M NaCl, 0.1% w/v $NaN_3$ and has a pH of 7.5.

In addition to the diluent, the calibrators and controls can also contain at least one buffer, at least one acid, at least one base, or combinations thereof. These buffers, bases or acids can be present in the calibrators and controls in addition to the buffers, bases and/or acids present in the diluent or as separate components if the diluent does not contain any buffers, bases and/or acids. Examples of buffers that can be used include, but are not limited to, acetate buffers (such as sodium acetate/acetic acid, potassium acetate/acetic acid), citrate buffers (such as sodium citrate/citric acid, potassium citrate/citric acid), phosphate buffers (such as mono-/di-sodium phosphate) or combinations thereof. Examples of acids that can be used include, but are not limited to, acetic acid, citric acid, diethylenetriaminepentaacetic acid (DTPA), hydrochloric acid (HCl) or combinations thereof. Examples of bases that can be used include, but are not limited to, sodium hydroxide. The amount of buffer, acid, base or combinations thereof in the calibrator or control can be from about 1 mM to about 500 mM, preferably in the amount of from about 5 to about 200 mM.

As mentioned above, the calibrators and controls of the present invention are stable and are in liquid form. The key to the stability of the calibrators and controls of the present invention is pH. More specifically, it has been discovered that the liquid calibrators and controls of the present invention are stable at a pH of from about 4.0 to about 6.5. Preferably, the pH of the liquid calibrators and controls of the present invention is from about 5.0 to about 6.0.

The calibrators and controls of the present invention having a pH of from about 4.0 to about 6.5 are stable for long periods of time and under a variety of storage conditions. For example, the calibrators and controls of the present invention remain stable when stored at temperatures of from about 2 to about 8° C. for a period of about twelve (12) months or more. The ability to store the calibrators and controls of the present invention at about 2° C. to about 8° C. is very convenient and allows for multiple-use of these reagents. In contrast, the frozen calibrators and controls known in the art are single-use reagents that have to be defrosted prior to conducting an assay. These calibrators and controls cannot be refrozen and have to be thrown away after being defrosted and used in an assay. Lyophilized controls known in the art, are only stable for 1 week at 2–8° C. after reconstitution and must be discarded.

Additionally, the calibrators and controls of the present invention having a pH of from about 4.0 to about 6.5 remain stable for several hours when used under laboratory conditions at ambient temperatures. Additionally, the calibrators and controls of the present invention are stable for limited periods of time (such as, but not limited to, about 1 minute to about 60 minutes, preferably for a period of about 20 minutes to about 30 minutes) when exposed to temperatures of from about 30 to about 40° C., preferably at a temperature of about 34° C.

In another embodiment, the present invention relates to methods for making stable calibrators and controls for use in ligand binding assays, such as immunoassays. The method of the present invention involves mixing at least one diluent with at least one natriuretic peptide to form a liquid calibrator or control. The diluent can have any of the compositions previously described herein and the natriuretic peptide can be any of the natriuretic peptides also previously described herein. Preferably, the diluent comprises at least one buffer having a good buffering capacity at the desired pH. Optionally, once the diluent has been prepared, it can optionally be heated to a temperature of from about 50 to about 60° C. for a period of from about 30 minutes to about 24 hours. Preferably, the diluent is heated in a water bath at a temperature of about 55° C. for a period of about 1 hour.

The diluent and natriuretic peptide are mixed together at a temperature of from about 15° C. to about 30° C., preferably at a temperature of from about 19° C. to about 23° C., until a homogenous solution is obtained. Once a homogenous liquid calibrator or control has been prepared, the pH is measured using a pH meter using techniques known in the art. If the pH of the liquid calibrator or control is determined to be in the range of from about 4.0 to about 6.5, then the pH of the liquid calibrator and control does not require any adjustment or stabilization and can be subjected to further processing steps such as those described in more detail below. However, if the pH of the liquid calibrator or control is not in the range of from about 4.0 to about 6.5, then the pH is adjusted or stabilized using routine techniques known in the art. For example, if the pH of the liquid calibrator or control is determined to be less than about 4.0, then at least one base, such as sodium hydroxide, at least one buffer, or combinations thereof, is added to the liquid calibrator or control in small quantities, preferably drop wise, and the pH measured repeatedly until the pH of the liquid calibrator or control is in the range of from about 4.0 to about 6.5. Likewise, if the pH of the liquid calibrator or control is determined to be greater than 6.5, then at least one buffer, at least one acid or combinations thereof is added to the liquid calibrator or control in small quantities, preferably drop wise, and the pH measured repeatedly until the pH of the liquid calibrator or control is in the range of from about 4.0 to about 6.5. Examples of buffers that can be used include, but are not limited to, acetate buffers (such as sodium acetate/acetic acid, potassium acetate/acetic acid), citrate buffers (such as sodium citrate/citric acid, potassium citrate/citric acid), phosphate buffers (such as mono-/di-sodium phosphate) or combinations thereof. Examples of acids that can be used include, but are not limited to, acetic acid, citric acid, diethylenetriaminepentaacetic acid, hydrochloric acid or combinations thereof.

Once a liquid calibrator or control having a pH in the range of from about 4.0 to about 6.5 has been prepared, then the calibrator or control can optionally be heated to a temperature of from about 50° to about 60° C. for a period of from about 30 minutes to about 24 hours. Preferably, the calibrator or control is heated in a water bath at a temperature of about 55° C. for a period of about 1 hour. After the calibrator or control has been heated, it can then be subjected to further processing steps such as those described below.

Once a liquid calibrator or control having a pH in the range of from about 4.0 to about 6.5 has been prepared, then the calibrator or control can be subjected to further processing steps, such as, but not limited to, vortexing and/or filtering, using techniques known in the art. Once these steps have been completed, then the calibrator or control is placed into bioclean or sterile vials (plastic or siliconized glass) and labeled accordingly. Once the calibrators or controls are placed into the bioclean or sterile vials, they can be stored for use in an assay at a temperature of from about 2° C. to about 8° C. for up to 12 months or more.

By way of example, and not of limitation, examples of the present invention will now be given.

EXAMPLE 1

BNP Immunoassay

Bulk diluents ("Dil") having the following formulations were prepared:
Experimental Control Diluent=4% BSA, 1% PEG, 0.1% Tween, 1% Dextran, 0.1% Proclin® 300, MEIA2 diluent.
Dil1=2% BSA, 0.1% Proclin® 300, MEIA2 diluent
Dil2=Same as Dil1.
Dil3=2% BSA, 0.1% ProClin® 300, MEIA2 diluent and 0.1% Tween.
Dil4=Same as Dil3.
Dil5=2% BSA, 0.1% ProClin® 300, MEIA2 diluent and 10 mM DTPA
Dil6—Same as Dil5.
Dil7=2% BSA, 0.1% ProClin® 300, MEIA2 diluent, 0.1% Tween, 10 mM DTPA.
Dil8=Same as Dil7.
Dil9=Same as Dil1.
Dil10=Same as Dil2.
Dil11=Same as Dil3.
Dil12=Same as Dil4.
Dil13=Same as Dil5.
Dil14=Same as Dil6.
Dil15=Same as Dil7.
Dil16=Same as Dil8.

After each of the above diluents was prepared, the pH was determined. The pH of diluents 7–16 was adjusted. Specifically, for diluents that did not contain DTPA, HCl was added (drop wise) to adjust the pH (to about 5.6). For the diluents that contained DTPA, NaOH was used to adjust the pH (to about 5.6 or 7.4). The pH was not adjusted for diluents 1–4. The final pH for each diluent is shown below in Table 1.

TABLE 1

| |
|---|
| Dil1 - pH 7.41 |
| Dil2 - pH 7.41* |
| Dil3 - pH 7.39 |
| Dil4 - pH 7.39* |
| Dil5 - pH 7.41 |
| Dil6 - pH 7.41* |
| Dil7 - pH 7.40 |
| Dil8 - pH 7.40* |
| Dil9 - pH 5.66 |
| Dil10 - pH 5.66* |
| Dil11 - pH 5.64 |
| Dil12 - pH 5.64* |
| Dil13 - pH 5.66 |
| Dil14 - pH 5.66* |
| Dil15 - pH 5.64 |
| Dil16 - pH 5.64* |

The pH of the experimental control diluent was 7.4.
*After final adjustment of the pH, these diluents (and the control) were also subjected to heat. Specifically, these diluents were heated in a water bath at a temperature of about 56° C. for about 1 hour.

Each of the above diluents was used to prepare three different calibrators containing different levels of human synthetic BNP (purchased from Peptide Institute (Osaka, Japan). Calibrator #A did not contain any human synthetic BNP. Calibrator #B contained 50 picograms/milliliter of human synthetic BNP. Calibrator #F contained 2000 picograms/milliliter of human synthetic BNP. Each calibrator was filtered and placed in calibrator bottles and stored at 37° C. for up to 14 days.

A BNP immunoassay was performed on an AxSYM® instrument (this instrument is described in U.S. Pat. No. 5,358,691). In addition to the calibrators prepared as described above, the following reagents were used in the assay:

1. Monoclonal antibody (MAb) 106.3 (capture antibody). This MAb binds to amino acids 5–13 on the BNP peptide. Monoclonal antibody 106.3 is commercially available from Scios, Inc. (Sunnyvale, Calif.) and is described in U.S. Pat. No. 6,376,207. A microparticle was coated with MAb 106.3 using the techniques described in U.S. Pat. No. 6,376,207, for use in the assay. Specifically, MAb 106.3 was coated onto 0.2 μm-size carboxylate modified polystyrene particles (commercially available from Seradyn, Inc., Indianapolis, Ind.) using EDAC coupling (EDAC is generally used as a carboxyl activating agent for amide bonding with primary amines. In addition, it reacts with phosphate groups. It is used in peptide synthesis, crosslinking proteins to nucleic acids and in preparing immunoconjugates. The chemical formula for EDAC is 1-ethyl-3-(3-dimethylaminopropyl) carbodiimide, hydrochloride. EDAC is commercially available from Interchim (France)). Particles were washed and overcoated with BSA. After a final wash, particles were stored at 2–8° C. in a buffer containing sucrose, sodium azide and BSA.

2. Monoclonal antibody BC203 (reporter antibody). This MAb binds to amino acids 27–32 on the BNP peptide. Monoclonal antibody BC203 is available from Shionogi, Inc. (Osaka, Japan). Monoclonal antibody BC203 is conjugated to alkaline phosphatase. BC203 was conjugated to alkaline phosphatase by Axis Shield Diagnostics (Dundee, Scotland, U.K.) in a typical coupling procedure using Traut's Reagent (which is 2-iminothiolane and is commercially available from Interchim (France)) and SMCC (SMCC is a heterobifunctional cross-linker whose formula is succinimidyl-4-(N-maleimidomethyl) cyclohexane-1-carboxylate. SMCC is commercially available from Interchim (France)). The stock conjugate was stored in a buffer containing BSA, fish gelatin, Brij-35 (Brij-35 is polyoxyethyleneglycol dodecyl ether and is a detergent that is commercially available from Sigma-Aldrich, St. Louis, Mo.) and sodium azide.

3,4-methylumbelliferyl phosphate substrate (1.2 mM, in buffer, containing 0.1 sodium azide), which is commercially available from Abbott Laboratories, Abbott Park, Ill.

4. The AxSYM® instrument system uses two (2) buffers: a Matrix Cell Wash and a Line Diluent. The Matrix Cell Wash is Tris buffered saline containing sodium azide and anti-microbial agents and is used to wash the particle reaction mixture. The Line Diluent is Phosphate buffer containing sodium azide and anti-microbial agents, and is used to rinse the AxSYM® probes in between each aspiration. The Matrix Cell Wash and Line Diluent are commercially available from Abbott Laboratories.

The 0.2 μm microparticles coated with the capture antibody in a buffer containing sucrose, sodium azide and BSA were pipetted by the sampling probe into the appropriate wells of the reaction vessel in the sampling center. An aliquot containing one of the calibrators described above in Table 1 was delivered to the same well of the reaction vessel as the microparticles to form a reaction mixture. The reaction vessel was transferred to the processing center. The reaction mixture was incubated for approximately 12 minutes at a temperature of about 34° C. After the incubation, an aliquot of the reaction mixture was transferred to the matrix cell of the AxSYM® instrument. The reaction mixture was then washed with the Matrix Cell Wash at 1 pulse of 100 μL to remove any of the calibrator that was not captured.

MAb BC203-conjugate at about 0.75 μg/mL in a buffer containing BSA, fish gelatin, Brij-3 and sodium azide, was dispensed onto the matrix cell and the resulting combination was incubated for approximately 12 minutes at a temperature of about 34° C. The matrix cell was washed with the Matrix Cell Wash at 5 pulses of 50 µL to remove the unbound materials.

A solution of the substrate, 4-methylumbelliferyl phosphate (MUP) in aminomethyl phosphate buffer (1.2 mM) was added to the matrix cell and the rate of formation of 4-methylumbelliferone was measured by fluorescence reflectance. The fluorescent product, 4-methylumbelliferone, was measured by the microparticle enzyme immunoassay (MEIA) optical assembly of the AxSYM® instrument.

Figure 1P:
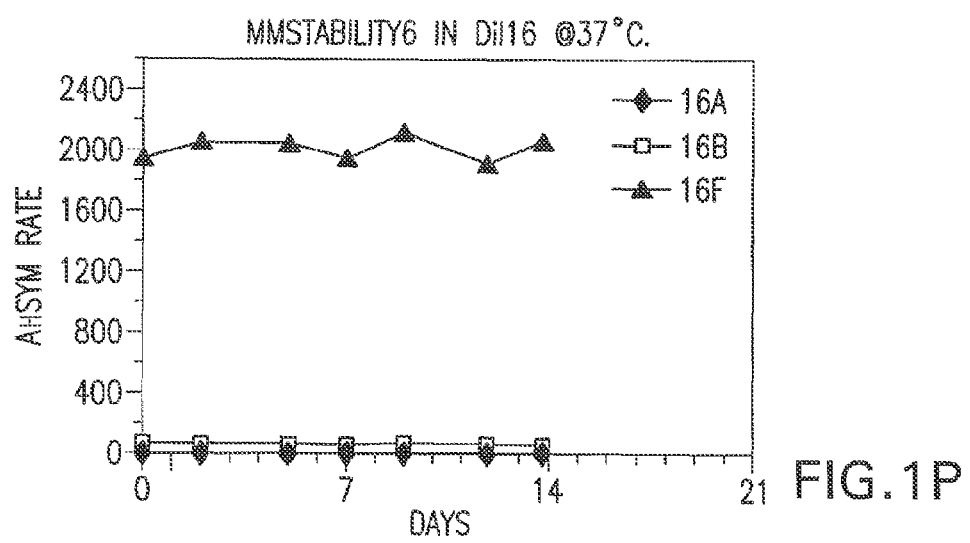

The AxSYM® system measured the alkaline phosphatase conversion of MUP to 4-methylumbelliferone (MU) by the rate of formation of the fluorescent product, MU. The aforementioned rates are typically measured in counts per second per second. The assay was conducted twice for each calibrator. The results in Table 2A below and FIGS. 1A-1P show the mean of the two assays.

TABLE 2A

Calibrator stability at accelerated stability condition (37° C.) for 0–14 days

| Cals | 0 | 2 | 5 | 7 | 9 | 12 | 14 |
|---|---|---|---|---|---|---|---|
| Con-A | 9.8 | 12.8 | 12.7 | 13.2 | 13.8 | 12.7 | 12.5 |
| Con-B | 39.9 | 41.6 | 37.9 | 39.4 | 37.8 | 33.8 | 30.9 |
| Con-F | 1725.2 | 1564.9 | 1410.1 | 1460.0 | 1477.6 | 1200.0 | 1107.9 |
| 1A | 9.8 | 10.6 | 11.4 | 11.8 | 12.8 | 11.7 | 12.5 |
| 1B | 37.3 | 33.6 | 30.6 | 30.2 | 32.9 | 29.2 | 26.4 |
| 1F | 1703.2 | 1370.2 | 1184.0 | 1256.6 | 1276.4 | 1192.1 | 1102.4 |
| 2A | 8.9 | 11.1 | 11.1 | 11.1 | 11.8 | 11.2 | 11.8 |
| 2B | 41.6 | 39.4 | 36.2 | 37.4 | 38.1 | 35.8 | 31.9 |
| 2F | 1865.9 | 1637.2 | 1398.4 | 1556.3 | 1562.7 | 1369.8 | 1309.2 |
| 3A | 10.7 | 11.3 | 13.2 | 13.9 | 11.7 | 13.7 | 13.3 |
| 3B | 34.4 | 39.9 | 33.6 | 37.9 | 36.0 | 34.0 | 31.7 |
| 3F | 1746.1 | 1500.2 | 1325.2 | 1427.5 | 1315.0 | 1139.1 | 1199.9 |
| 4A | 10.5 | 11.2 | 12.0 | 11.6 | 12.5 | 12.6 | 12.4 |
| 4B | 32.8 | 39.6 | 33.9 | 36.2 | 36.9 | 32.5 | 32.7 |
| 4F | 1611.8 | 1531.2 | 1236.9 | 1435.9 | 1418.2 | 1234.7 | 1190.8 |
| 5A | 9.2 | 11.4 | 12.3 | 12.0 | 11.9 | 12.1 | 12.3 |
| 5B | 37.4 | 38.7 | 34.8 | 40.1 | 38.1 | 36.1 | 32.3 |

TABLE 2A-continued

Calibrator stability at accelerated stability condition (37° C.) for 0–14 days

| Cals | 0 | 2 | 5 | 7 | 9 | 12 | 14 |
|---|---|---|---|---|---|---|---|
| 5F | 1671.1 | 1519.9 | 1285.2 | 1546.7 | 1444.3 | 1290.9 | 1246.3 |
| 6A | 10.4 | 11.3 | 12.6 | 12.2 | 13.1 | 13.2 | 11.7 |
| 6B | 38.7 | 38.1 | 37.1 | 38.1 | 39.0 | 33.9 | 32.1 |
| 6F | 1721.3 | 1570.1 | 1350.8 | 1548.5 | 1455.7 | 1285.7 | 1387.7 |
| 7A | 11.4 | 13.0 | 13.7 | 13.0 | 13.5 | 15.3 | 13.9 |
| 7B | 44.8 | 47.3 | 41.5 | 45.5 | 47.0 | 39.0 | 38.3 |
| 7F | 2036.9 | 1783.4 | 1531.5 | 1767.9 | 1787.4 | 1541.1 | 1483.2 |
| 8A | 10.3 | 12.2 | 12.8 | 14.4 | 13.9 | 14.6 | 13.4 |
| 8B | 38.5 | 43.5 | 35.4 | 39.4 | 39.8 | 35.6 | 35.1 |
| 8F | 1637.5 | 1605.5 | 1305.2 | 1449.6 | 1468.7 | 1294.0 | 1286.0 |
| 9A | 10.7 | 11.7 | 12.6 | 14.1 | 14.7 | 12.6 | 13.0 |
| 9B | 43.8 | 55.9 | 47.8 | 50.1 | 54.1 | 49.0 | 45.2 |
| 9F | 1807.9 | 2072.7 | 1707.4 | 1867.6 | 1998.2 | 1713.0 | 1634.9 |
| 10A | 10.1 | 12.0 | 12.5 | 13.2 | 13.4 | 12.6 | 12.1 |
| 10B | 48.7 | 55.8 | 49.7 | 51.9 | 59.2 | 48.5 | 46.5 |
| 10F | 1794.0 | 2124.1 | 1928.3 | 1839.6 | 2142.1 | 1812.5 | 1648.3 |
| 11A | 11.0 | 11.4 | 13.3 | 14.0 | 14.0 | 14.3 | 12.9 |
| 11B | 39.0 | 49.0 | 42.8 | 43.5 | 49.2 | 43.4 | 42.2 |
| 11F | 1606.1 | 1887.1 | 1593.5 | 1633.5 | 1836.5 | 1529.1 | 1637.9 |
| 12A | 10.0 | 12.2 | 12.9 | 13.6 | 13.4 | 13.0 | 12.7 |
| 12B | 44.4 | 58.0 | 46.4 | 49.4 | 53.7 | 48.4 | 48.6 |
| 12F | 1784.8 | 1993.3 | 1759.2 | 1740.2 | 1839.2 | 1614.6 | 1629.7 |
| 13A | 10.1 | 11.9 | 12.2 | 12.2 | 12.9 | 12.2 | 12.6 |
| 13B | 49.2 | 64.1 | 58.2 | 58.7 | 62.1 | 54.0 | 54.4 |
| 13F | 1996.7 | 2283.9 | 2023.6 | 2088.8 | 2283.5 | 1983.7 | 2171.4 |
| 14A | 10.6 | 12.4 | 12.5 | 12.1 | 13.3 | 12.0 | 13.1 |
| 14B | 42.7 | 56.4 | 54.0 | 56.5 | 56.8 | 47.8 | 52.6 |
| 14F | 1864.3 | 2029.9 | 1861.4 | 1932.5 | 2064.8 | 1832.9 | 2092.6 |
| 15A | 11.7 | 13.6 | 13.2 | 14.0 | 16.4 | 15.5 | 13.0 |
| 15B | 49.8 | 62.7 | 54.7 | 58.2 | 59.1 | 56.5 | 55.4 |
| 15F | 2106.2 | 2259.1 | 1995.2 | 2032.4 | 2247.6 | 2062.1 | 2150.2 |
| 16A | 12.0 | 12.8 | 12.7 | 13.5 | 16.3 | 14.8 | 15.0 |
| 16B | 44.8 | 57.0 | 50.3 | 52.4 | 60.5 | 48.4 | 54.1 |
| 16F | 1801.6 | 1889.1 | 1889.4 | 1794.1 | 1977.2 | 1738.8 | 1930.6 |

Based upon the results shown about in Table 2A, the stability of calibrators 13, 14, 15 and 16 further examined at 21 days, 35 days, 49 days, 77 days, 96 days and 187 days. The results are shown below in Table 2B. The results shown are the mean of two assays.

TABLE 2B

| | 21 | 35 | 49 | 77 | 96 | 110 | 125 | 131 | 159 | 187 |
|---|---|---|---|---|---|---|---|---|---|---|
| Con-A | 13.7 | 14.8 | 14.9 | | | | | | | |
| Con-B | 27.5 | 26.6 | 24.1 | | | | | | | |
| Con-F | 992.2 | 795.4 | 650.6 | | | | | | | |
| 13A | 13.4 | 13.8 | 13.4 | 14.8 | 20.6 | | | | | |
| 13B | 46.8 | 48.6 | 50.0 | 45.4 | 46.6 | | | | | |
| 13F | 1853.7 | 1895.4 | 1803.3 | 1579.1 | 1484.3 | | | | | |
| 14A | 11.1 | 15.2 | 14.3 | 15.6 | 20.5 | | | | | |
| 14B | 42.8 | 49.2 | 44.7 | 40.9 | 42.7 | | | | | |
| 14F | 1712.0 | 1736.8 | 1694.1 | 1428.1 | 1291.5 | | | | | |
| 15A | #N/A | #N/A | #N/A | #N/A | #N/A | #N/A | #N/A | #N/A | #N/A | 18.0 |
| 15B | #N/A | #N/A | #N/A | #N/A | #N/A | #N/A | #N/A | #N/A | #N/A | 42.6 |
| 15F | #N/A | #N/A | #N/A | #N/A | #N/A | #N/A | #N/A | #N/A | #N/A | 1297.3 |
| 16A | 12.8 | 16.0 | 15.1 | 16.6 | 20.9 | #N/A | #N/A | #N/A | #N/A | 18.7 |
| 16B | 43.8 | 49.4 | 42.9 | 46.1 | 45.3 | #N/A | #N/A | #N/A | #N/A | 34.8 |
| 16F | 1775.0 | 1646.2 | 1673.6 | 1490.2 | 1350.2 | #N/A | #N/A | #N/A | #N/A | 1030.6 |

The data in Table 2A and FIGS. 1A-1P demonstrate that calibrators having a pH in the range of from about 4.0 to about 6.5, particularly at pH 5.6, exhibited enhanced accelerated stability compared to similar formulations with a pH of about 7.4. In calibrators 1–8 and the experimental control diluent calibrator, the rates for the "F" calibrators, i.e., 1F, 2F, 3F, 4F, 5F, etc. (hereinafter referred to as the "Cal-F" rates) fell much faster through 14 days of stability study than the Cal-F rates in calibrators 9–16 which were similar formulations but at a different pH.

The enhanced accelerated stability can be quantified by comparing the average percentage change in F Calibrator rates at 37° C. for 14 days for the eight F Calibrators at approximately pH 7.4 (Calibrators 1F–8F; mean F Calibrator rate decreased by 27.1%) versus the eight F Calibrators in similar formulations but at approximately pH 5.6 (Calibrators 9F–16F; mean F Calibrator rate increased 0.9%). In each paired calibrator diluent (e.g., 1 and 9, 2 and 10, etc.) in which the formulation is identical except for pH, the F Calibrator rates dropped more for those at approximately pH 7.4 than those at approximately pH 5.6. (Accelerated stability studies are well known in the art in which materials are stressed at a higher temperature than the intended storage condition. In describing a European standard for stability testing of in vitro diagnostic medical devices (EN 13640:2002), Armstrong describes incubation at an elevated temperature of 25° C., 37° C. or 40° C. as examples of accelerated stability testing. The Food and Drug Administration also recognizes accelerated stability studies, for example, the Center for Drug Evaluation and Research, Manual of Policies and Procedures, issued directive MAPP 5226.1. Reaffirmation of expiration dating period for abbreviated applications. In the background section of this directive they describe accelerated stability conditions and data submittable for supporting stability (expiration dating) of generic drugs.)

EXAMPLE 2

BNP Immunoassay

Bulk diluents ("Dil") of the following formulations were prepared.
Experimental Control Diluent=4% BSA, 1% PEG, 0.1% Tween, 1% Dextran, 0.1%
Proclin® 300, MEIA2 diluent.
Dil1=2% BSA, 0.1% Proclin® 300, MEIA2 diluent
Dil2=Same as Dil1.
Dil3=2% BSA, 0.1% Proclin® 300, MEIA2 diluent and 0.1% Tween.
Dil4=Same as Dil3.
Dil5=2% BSA, 0.1% Proclin® 300, MEIA2 diluent and 10 mM DTPA
Dil6—Same as Dil5.
Dil7=2% BSA, 0.1% Proclin® 300, MEIA2 diluent, 0.1% Tween, 10 mM DTPA.
Dil8=Same as Dil7.
Dil9=Same as Dil1.
Dil10=Same as Dil2.
Dil11=Same as Dil3.
Dil12=Same as Dil4.
Dil13=Same as Dil5.
Dil14=Same as Dil6.
Dil15=Same as Dil7.
Dil16=Same as Dil8.

After each of the above diluents was prepared, the pH was determined. The pH of diluents 7–16 was adjusted. Specifically, for diluents that contained DTPA, NaOH was added (drop wise) to adjust the pH (to about 5.6). For the diluents that contained DTPA, NaOH was used to adjust the pH (to about 5.6 or 7.4). The pH was not adjusted for diluents 1–4. The final pH for each diluent is shown below in Table 3.

TABLE 3

| |
|---|
| Dil1 - pH 7.41 |
| Dil2 - pH 7.41* |
| Dil3 - pH 7.39 |
| Dil4 - pH 7.39* |
| Dil5 - pH 7.41 |
| Dil6 - pH 7.41* |
| Dil7 - pH 7.40 |
| Dil8 - pH 7.40* |
| Dil9 - pH 5.66 |
| Dil10 - pH 5.66* |
| Dil11 - pH 5.64 |
| Dil12 - pH 5.64* |
| Dil13 - pH 5.66 |
| Dil14 - pH 5.66* |
| Dil15 - pH 5.64 |
| Dil16 - pH 5.64* |

The pH of the experimental control diluent was 7.4.
*After final adjustment of the pH, these diluents (and the control) were also subjected to heat. Specifically, these diluents were heated in a water bath at a temperature of about 56° C. for about 1 hour.

Each of the above diluents was used to prepare three different calibrators containing different levels of human synthetic BNP (purchased from Peptide Institute (Osaka, Japan). Calibrator #A did not contain any human synthetic BNP. Calibrator #B contained 50 picograms/milliliter of human synthetic BNP. Calibrator #F contained 2000 picograms/milliliter of human synthetic BNP. Each calibrator was filtered and placed in calibrator bottles and stored at 2–8° C. for up to 271 days.

Figure 2A:
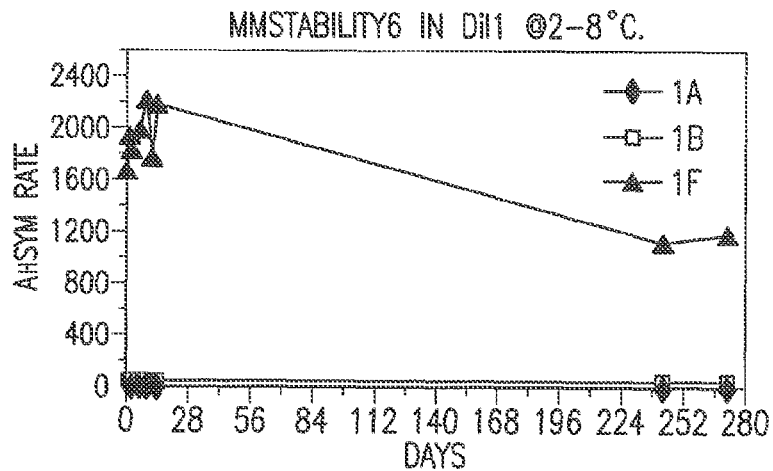
FIGS. 2A-2P shows graphs demonstrating the stability of calibrators having varying pH's at 2–8° C. over time.
Figure 2B:
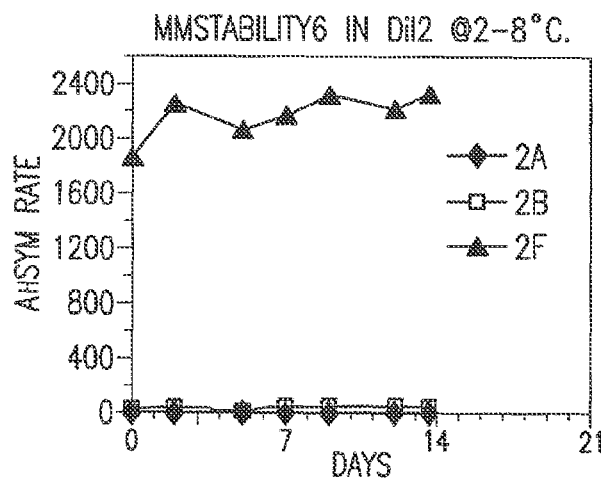
Figure 2C:
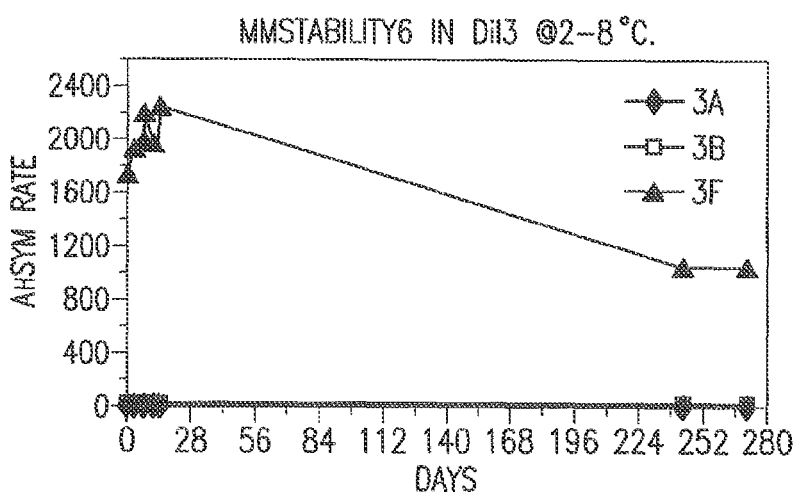
Figure 2D:
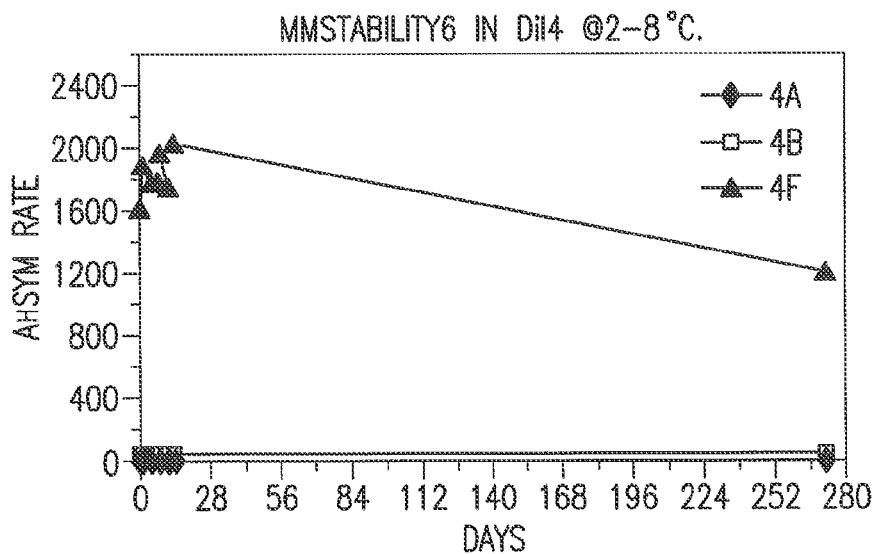
Figure 2E:
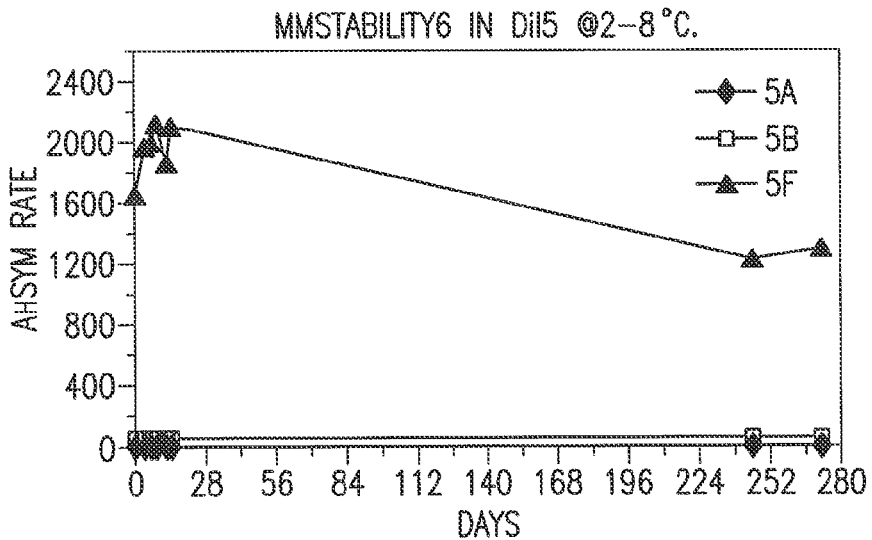
Figure 2F:
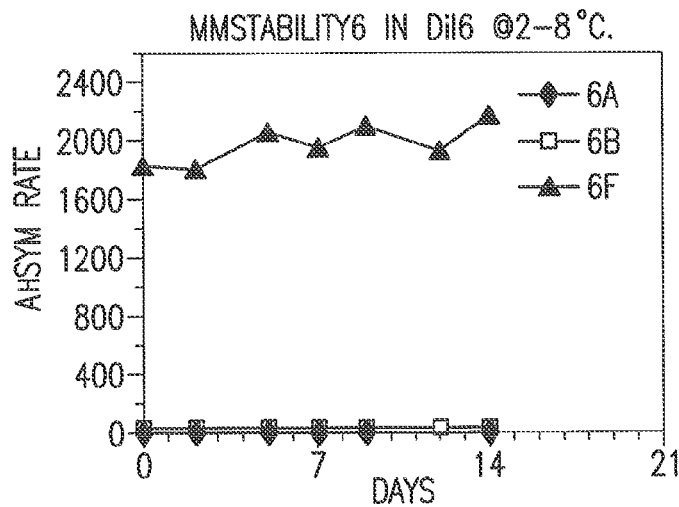
Figure 2G:
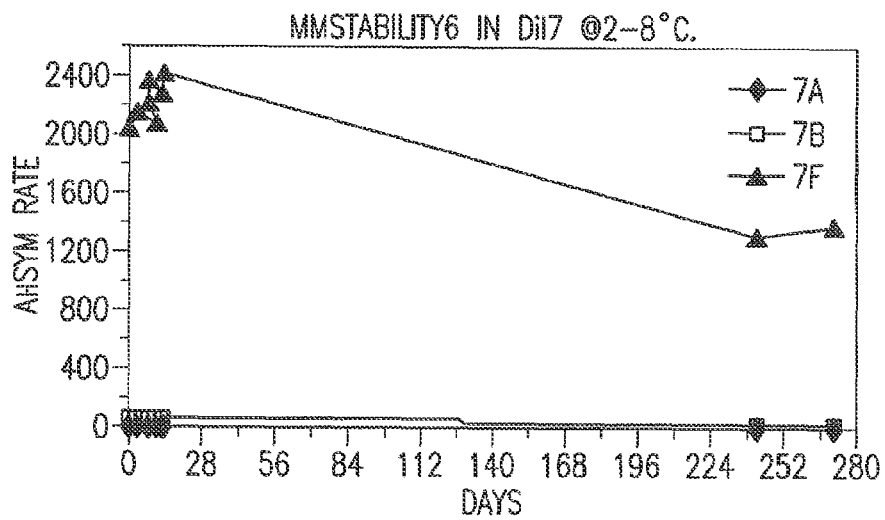
Figure 2H:
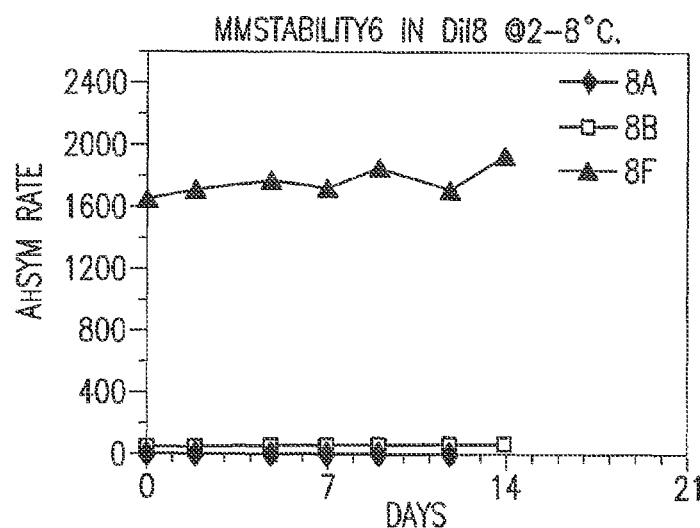
Figure 2I:
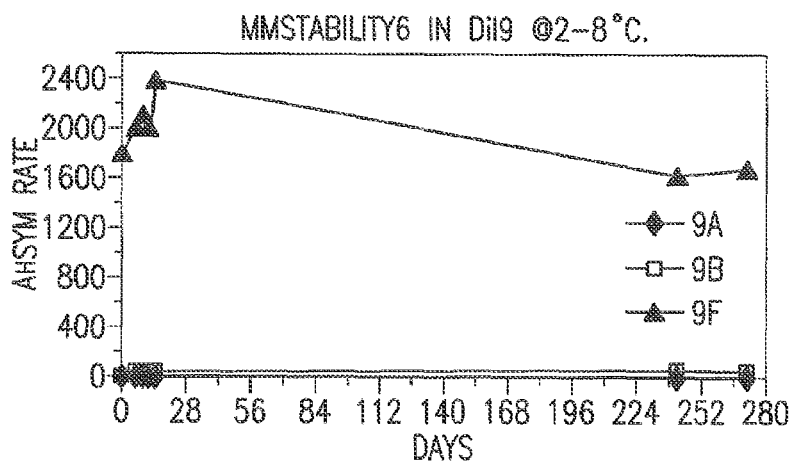
Figure 2J:
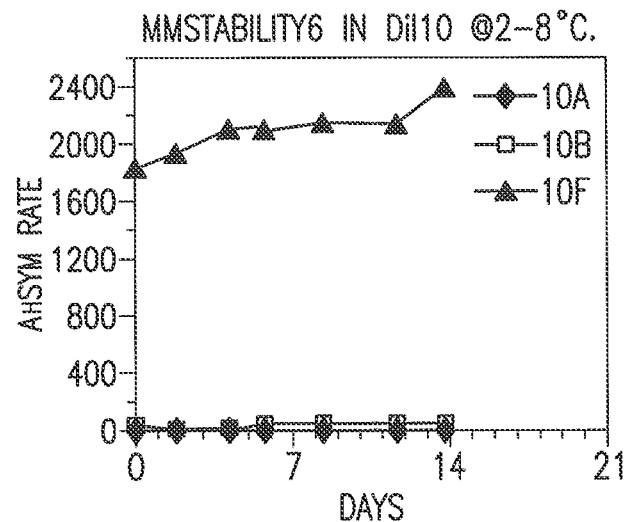
Figure 2K:
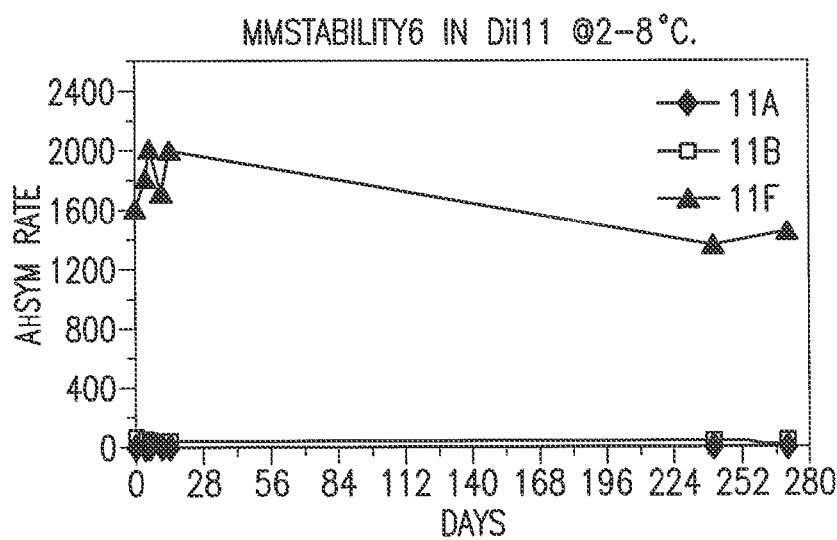
Figure 2L:
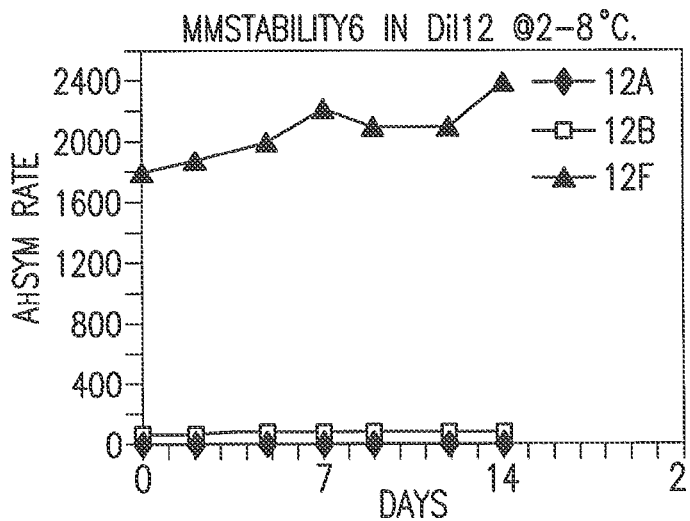
Figure 2M:
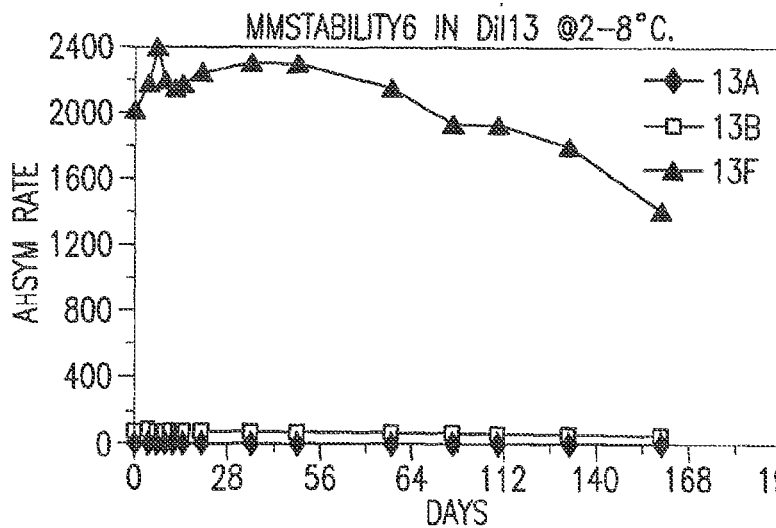
Figure 2N:
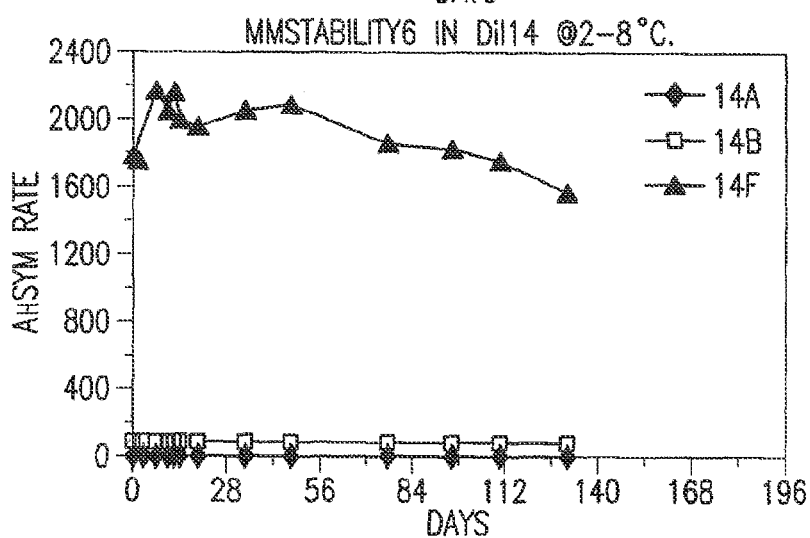
Figure 2O:
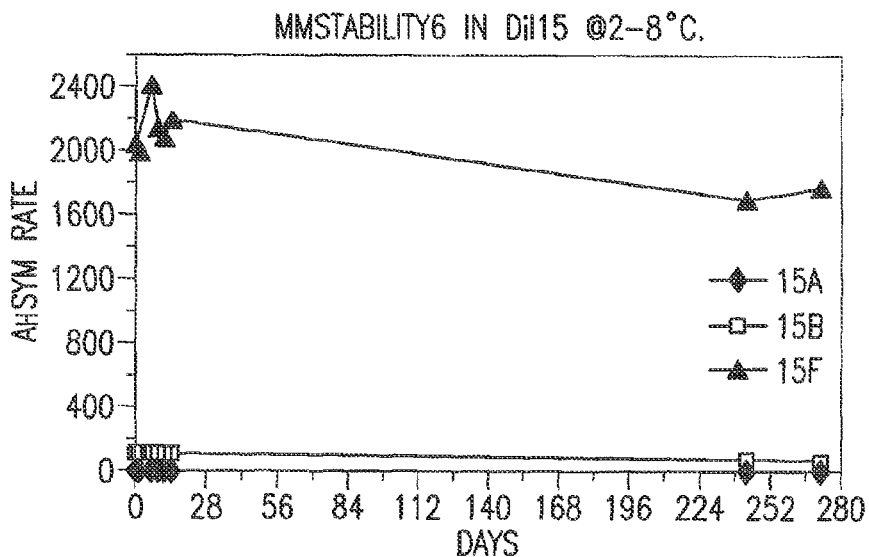
Figure 2P:
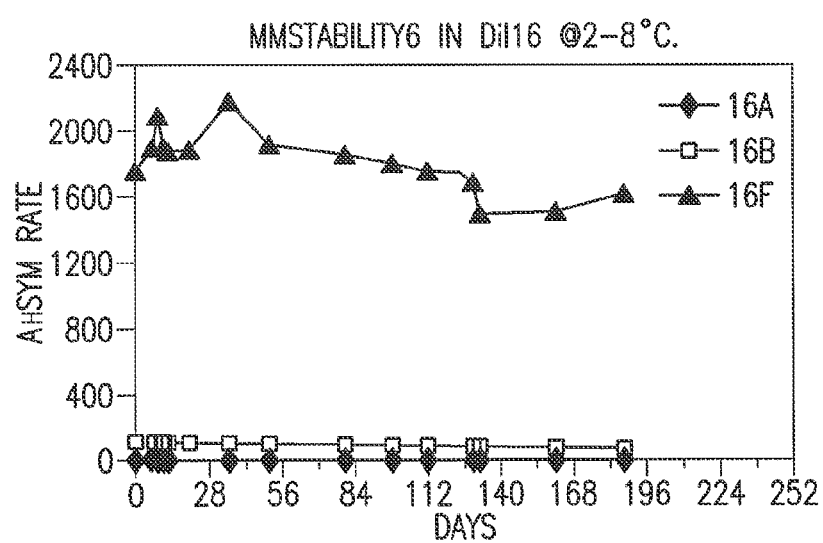

A BNP immunoassay was performed on an AxSYM® instrument as described in Example 1. The assay was conducted twice for each calibrator. The results in Table 4 below and FIGS. 2A-2P show the mean of two assays.

TABLE 4

| | Calibrator stability at 2–8° C. for up to 271 days | | | | | | | |
|---|---|---|---|---|---|---|---|---|
| Cals | 0 | 2 | 5 | 7 | 9 | 12 | 14 | 243 | 271 |
| Con-A | 9.8 | 13.2 | 12.3 | 14.6 | 14.8 | 14.8 | 14.4 | 19.9 | 16.4 |
| Con-B | 39.9 | 52.7 | 48.3 | 54.3 | 57.9 | 51.0 | 58.3 | 43.8 | 39.9 |
| Con-F | 1725.2 | 1988.8 | 1867.6 | 1949.6 | 2229.4 | 1901.8 | 2123.8 | 1199.9 | 1239.2 |
| 1A | 9.8 | 12.7 | 11.5 | 12.8 | 12.9 | 11.9 | 11.8 | 20.7 | 15.3 |
| 1B | 37.3 | 49.4 | 45.3 | 50.2 | 51.4 | 46.5 | 52.8 | 39.0 | 36.4 |
| 1F | 1703.2 | 1928.9 | 1887.0 | 2004.1 | 2183.3 | 1846.8 | 2196.8 | 1125.8 | 1181.3 |
| 2A | 8.9 | 11.6 | 11.7 | 12.3 | 12.6 | 11.5 | 11.5 | | |
| 2B | 41.6 | 52.4 | 50.0 | 56.6 | 63.8 | 53.8 | 57.7 | | |

TABLE 4-continued

Calibrator stability at 2–8° C. for up to 271 days

| Cals | 0 | 2 | 5 | 7 | 9 | 12 | 14 | 243 | 271 |
|---|---|---|---|---|---|---|---|---|---|
| 2F | 1865.9 | 2255.0 | 2055.9 | 2170.1 | 2298.1 | 2186.9 | 2327.8 | | |
| 3A | 10.7 | 12.1 | 12.4 | 13.0 | 14.6 | 15.6 | 14.4 | 21.7 | 17.2 |
| 3B | 34.4 | 47.1 | 43.9 | 52.3 | 49.6 | 48.3 | 51.5 | 39.6 | 36.8 |
| 3F | 1746.1 | 1940.5 | 1919.3 | 2103.5 | 2173.1 | 1879.1 | 2232.9 | 1021.9 | 1030.5 |
| 4A | 10.5 | 11.8 | 12.5 | 13.7 | 14.8 | 15.3 | 14.0 | #N/A | 16.8 |
| 48 | 32.8 | 42.6 | 42.8 | 45.4 | 47.1 | 44.9 | 48.6 | #N/A | 39.6 |
| 4F | 1611.8 | 1863.5 | 1792.4 | 1859.7 | 1973.7 | 1781.1 | 2026.9 | #N/A | 1190.4 |
| 5A | 9.2 | 12.0 | 12.1 | 13.9 | 12.3 | 12.0 | 12.2 | 21.1 | 15.1 |
| 5B | 37.4 | 46.7 | 43.6 | 48.8 | 55.5 | 48.8 | 50.9 | 44.0 | 39.9 |
| 5F | 1671.1 | 1989.7 | 1907.4 | 1976.4 | 2133.1 | 1910.4 | 2110.1 | 1230.4 | 1319.5 |
| 6A | 10.4 | 12.8 | 11.6 | 13.3 | 12.7 | 12.5 | 13.7 | | |
| 6B | 38.7 | 44.9 | 43.8 | 46.3 | 50.0 | 45.2 | 50.9 | | |
| 6F | 1721.3 | 1710.0 | 1906.6 | 1845.7 | 1954.2 | 1791.3 | 2027.4 | | |
| 7A | 11.4 | 13.3 | 15.2 | 16.4 | 14.1 | 15.0 | 14.6 | 24.1 | 19.2 |
| 7B | 44.8 | 52.7 | 60.2 | 58.5 | 63.7 | 56.5 | 65.4 | 48.0 | 41.5 |
| 7F | 2036.9 | 2120.2 | 2150.2 | 2205.2 | 2340.9 | 2138.6 | 2405.4 | 1329.9 | 1386.0 |
| 8A | 10.3 | 13.0 | 12.9 | 15.1 | 14.2 | 16.0 | 14.6 | | |
| 8B | 38.5 | 43.2 | 46.6 | 49.6 | 51.9 | 49.0 | 55.3 | | |
| 8F | 1637.5 | 1700.3 | 1765.6 | 1728.0 | 1856.6 | 1703.4 | 1963.0 | | |
| 9A | 10.7 | 13.5 | 12.9 | 13.5 | 12.6 | 11.6 | 12.3 | 21.5 | 16.3 |
| 9B | 43.8 | 51.5 | 56.6 | 54.4 | 60.1 | 56.5 | 61.9 | 55.7 | 50.4 |
| 9F | 1807.9 | 1855.8 | 1985.5 | 2042.5 | 2078.3 | 2012.2 | 2382.1 | 1586.5 | 1669.1 |
| 10A | 10.1 | 11.8 | 12.1 | 12.3 | 12.9 | 12.1 | 11.3 | | |
| 10B | 48.7 | 50.4 | 50.4 | 54.7 | 56.6 | 56.0 | 65.1 | | |
| 10F | 1794.0 | 1922.5 | 2119.9 | 2051.4 | 2153.9 | 2130.1 | 2387.8 | | |
| 11A | 11.0 | 12.5 | 12.1 | 13.4 | 14.9 | 14.5 | 14.6 | 22.5 | 16.9 |
| 11B | 39.0 | 42.9 | 46.7 | 51.3 | 53.9 | 46.4 | 54.0 | 50.2 | 45.8 |
| 11F | 1606.1 | 1606.4 | 1864.1 | 1942.5 | 1894.7 | 1740.9 | 1992.9 | 1361.7 | 1444.0 |
| 12A | 10.0 | 12.3 | 13.0 | 14.9 | 14.6 | 14.3 | 14.5 | | |
| 12B | 44.4 | 49.4 | 57.5 | 62.8 | 58.5 | 54.4 | 62.9 | | |
| 12F | 1784.8 | 1844.2 | 1999.4 | 2206.1 | 2074.8 | 2072.6 | 2389.0 | | |
| 13A | 10.1 | 11.8 | 12.8 | 11.1 | 12.0 | 12.4 | 11.0 | | |
| 13B | 49.2 | 53.9 | 62.3 | 69.2 | 62.3 | 61.3 | 65.1 | | |
| 13F | 1996.7 | 2037.5 | 2187.6 | 2382.9 | 2225.7 | 2148.3 | 2168.7 | | |
| 14A | 10.6 | 11.5 | 13.1 | 13.8 | 12.3 | 12.9 | 12.5 | | |
| 14B | 42.7 | 48.6 | 56.0 | 62.2 | 54.0 | 51.7 | 51.6 | | |
| 14F | 1864.3 | 1820.8 | 2135.9 | 2194.2 | 2090.4 | 2093.0 | 2000.9 | | |
| 15A | 11.7 | 13.8 | 14.4 | 13.8 | 15.5 | 14.2 | 15.3 | 22.2 | 17.7 |
| 15B | 49.8 | 54.5 | 63.3 | 68.2 | 61.8 | 61.9 | 57.2 | 55.9 | 53.2 |
| 15F | 2106.2 | 2059.9 | 2354.6 | 2414.5 | 2191.5 | 2130.9 | 2209.0 | 1722.8 | 1805.3 |
| 16A | 12.0 | 12.2 | 14.0 | 15.2 | 14.7 | 14.3 | 14.2 | 21.8 | DEPLETED |
| 16B | 44.8 | 48.0 | 53.0 | 59.9 | 55.1 | 53.3 | 54.5 | 50.5 | DEPLETED |
| 16F | 1801.6 | 1760.3 | 1943.0 | 2093.6 | 1907.9 | 1866.5 | 1861.8 | #N/A | DEPLETED |

The data in Table 4 and FIGS. 2A-2P demonstrate that calibrators having a pH in the range of from about 4.0 to about 6.5 (calibrators 9–16) exhibited less of a signal decrease than the corresponding calibrators 1–8 at a pH of about 7.4. This enhanced long term stability was observed through 271 days at 2–8° C.

EXAMPLE 3

BNP Immunoassay

Bulk diluents ("Dil") of the following formulations were prepared.
Dil1=2% BSA, 0.1% Proclin® 300, 10 mM DTPA
Dil2=2% BSA, 0.1% Proclin® 300, 10 mM DTPA, 100 mM NaCl, 0.1% sodium azide in water
Dil3=2% BSA, 0.1% Proclin® 300, 10 mM DTPA, 100 mM NaCl, 0.1% sodium azide in water
Dil4=2% BSA, 0.1% Proclin® 300, 10 mM DTPA, 100 mM NaCl, 0.1% sodium azide in water
Dil5=2% BSA, 0.1% Proclin® 300, 10 mM DTPA, 100 mM NaCl, 0.1% sodium azide in water
Dil6=2% BSA, 0.1% Proclin® 300, 10 mM DTPA, 100 mM NaCl, 0.1% sodium azide in water
Dil7=2% BSA, 0.1% Proclin® 300, 10 mM DTPA, 100 mM NaCl, 0.1% sodium azide in water
Dil8=2% BSA, 0.1% Proclin® 300, 10 mM DTPA, 100 mM NaCl, 0.1% sodium azide in water
Dil9=2% BSA, 0.1% Proclin® 300, 10 mM DTPA, 100 mM NaCl, 0.1% sodium azide in water
Dil10=2% BSA, 0.1% Proclin® 300, 10 mM DTPA, 100 mM NaCl, 0.1% sodium azide in water In addition, to the components listed above, diluent 1 also contained MEIA2 as a base diluent. Diluents 3–6 also contained a solution of sodium acetate and a solution of acetic acid. Diluents 7–10 also contained a solution of monobasic sodium phosphate and a solution of dibasic sodium phosphate.

After each of the above diluents was prepared, the pH was determined. The pH of diluents 3–10 was adjusted. Specifically, the pH of diluents 3–10 was adjusted with NaOH. The pH was not adjusted for diluents 1–2. The final pH for each diluent is shown below in Table 5.

TABLE 5

Dil1 - pH 5.66*
Dil2 - pH 3.91
Dil3 - pH 3.47
Dil4 - pH 4.50
Dil5 - pH 5.02
Dil6 - pH 5.49*
Dil7 - pH 6.10*
Dil8 - pH 6.51*
Dil9 - pH 7.04*
Dil10 - pH 10.04*

*After final adjustment of the pH, these diluents were also subjected to heat. Specifically, these diluents were heated in a water bath at a temperature of about 60° C. for about 1 hour.

Each of the above diluents was used to prepare three different calibrators containing different levels of human synthetic BNP (purchased from Peptide Institute (Osaka, Japan). Calibrator #A did not contain any human synthetic BNP. Calibrator #B contained 50 picograms/milliliter of human synthetic BNP. Calibrator #F contained 2000 picograms/milliliter of human synthetic BNP. Each calibrator was filtered and placed in calibrator bottles and stored at 37° C. and 2–8° C. for up to 252 days.

Figure 3A:
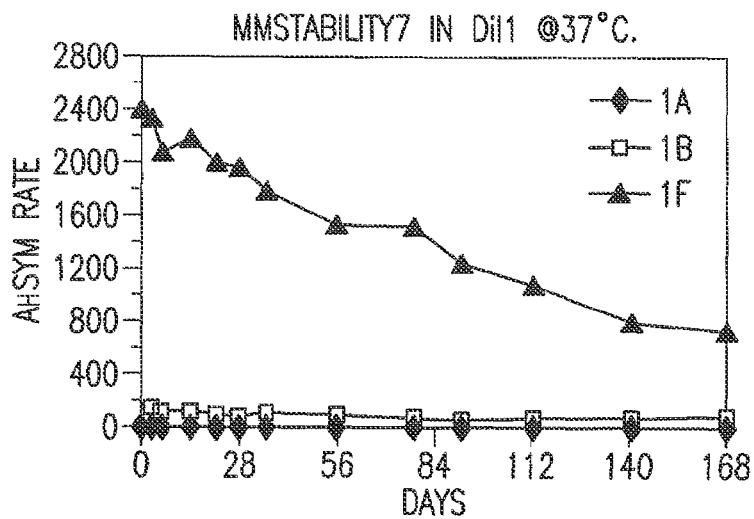
FIGS. 3A-3T shows graphs demonstrating the stability of calibrators having varying pH's at 37° C. and 2–8° C. over time.
Figure 3B:
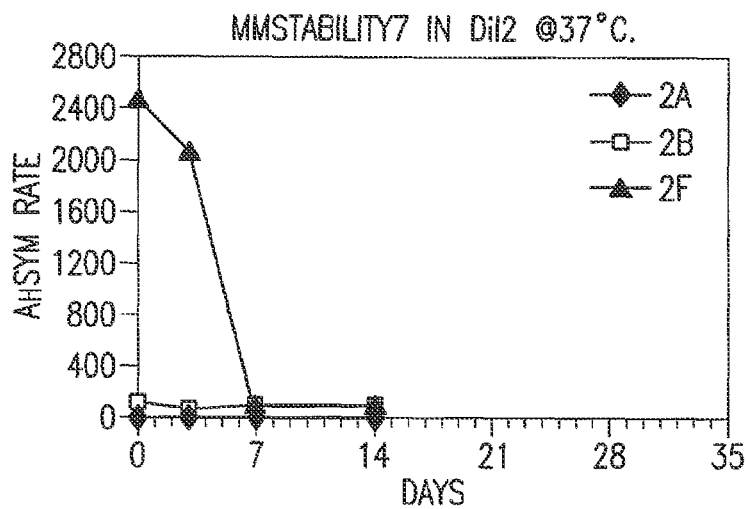
Figure 3C:
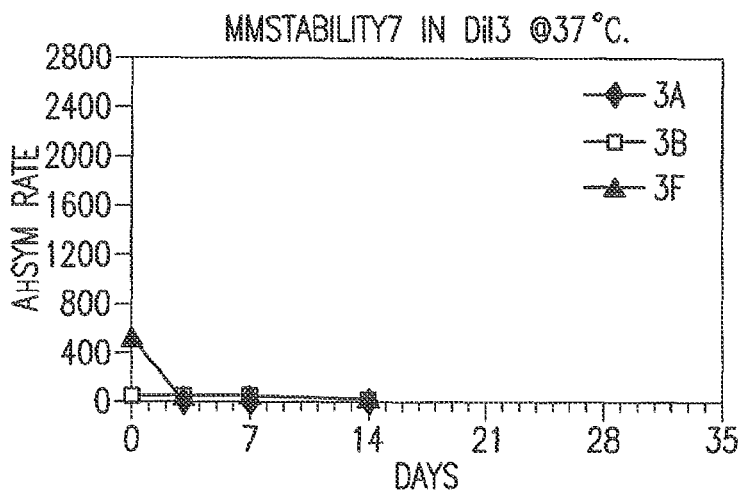
Figure 3D:
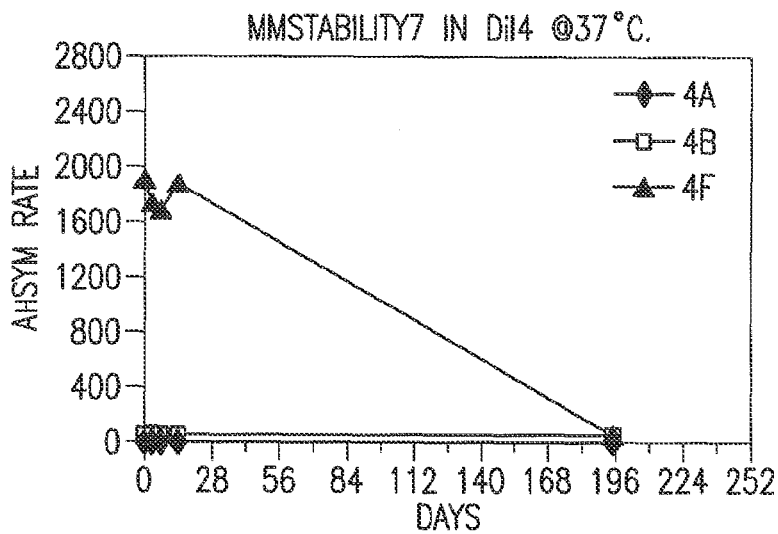
Figure 3E:
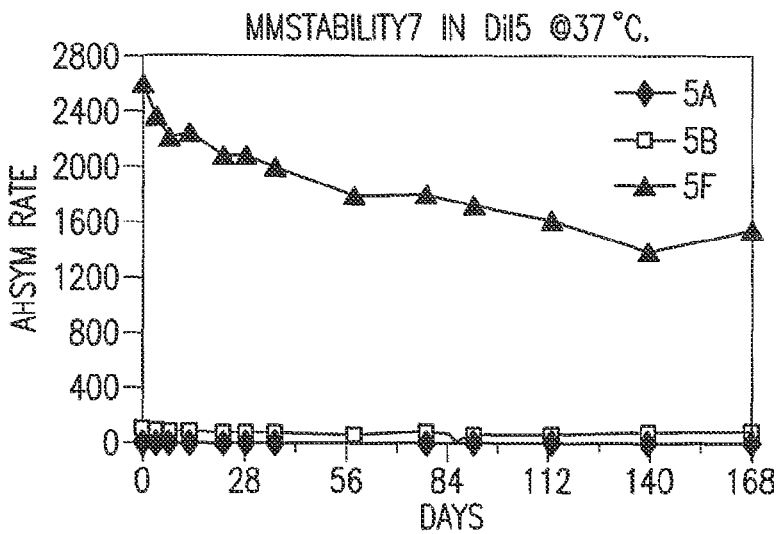
Figure 3F:
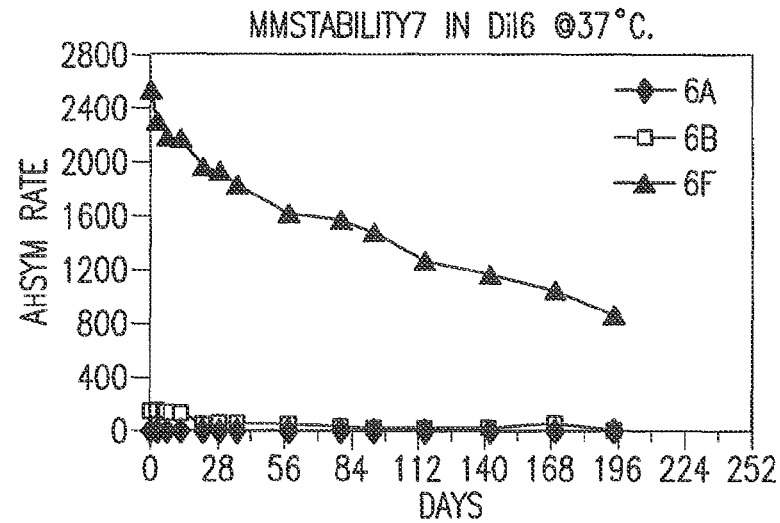
Figure 3G:
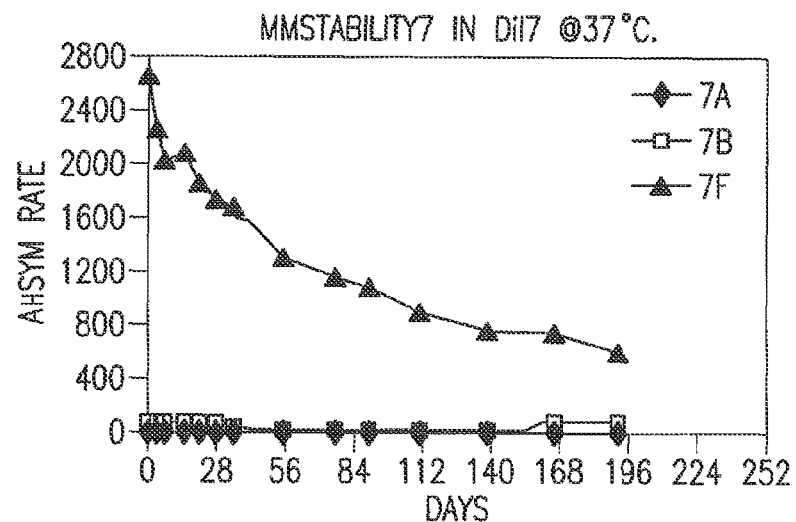
Figure 3H:
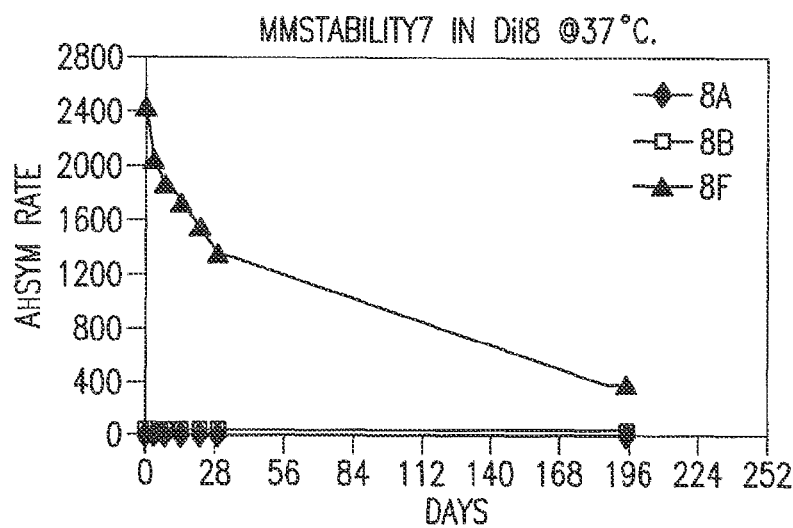
Figure 3I:
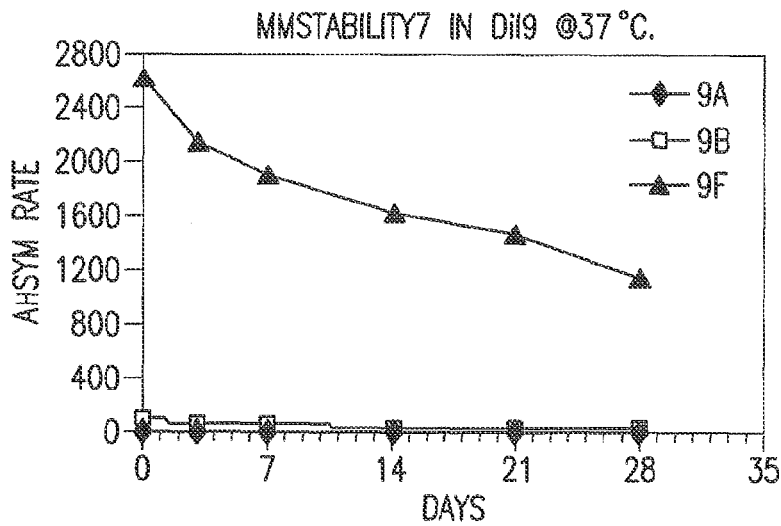
Figure 3J:
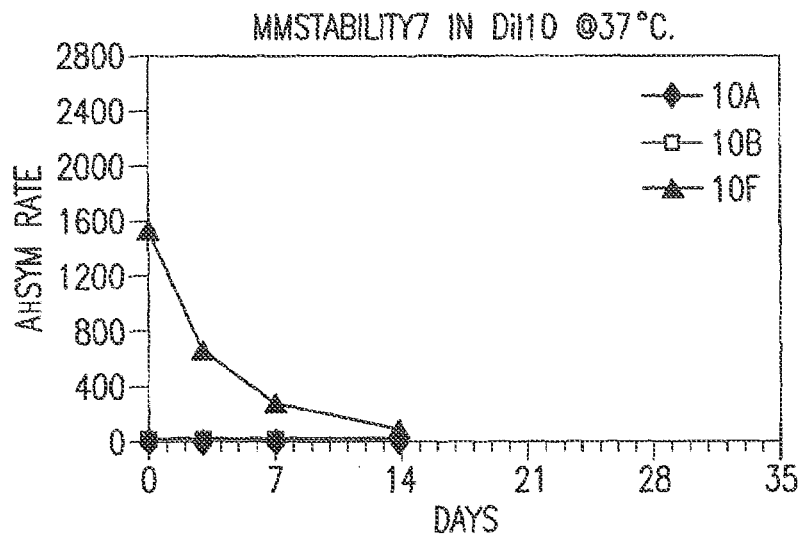
Figure 3K:
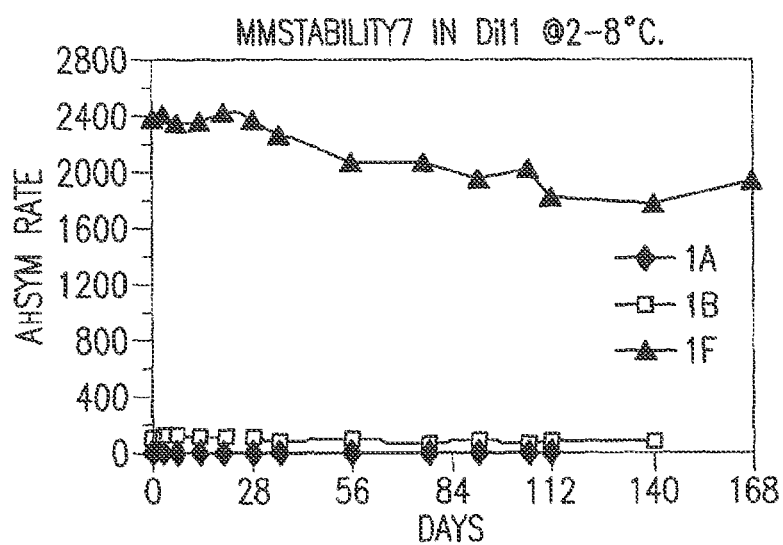
Figure 3L:
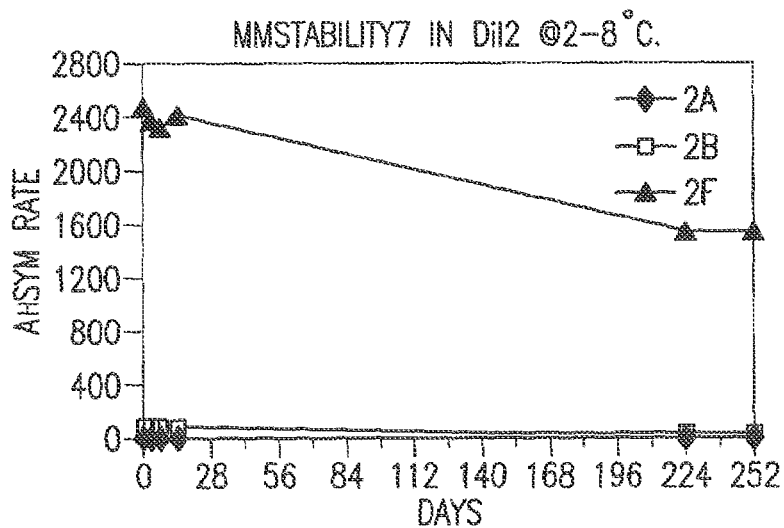
Figure 3M:
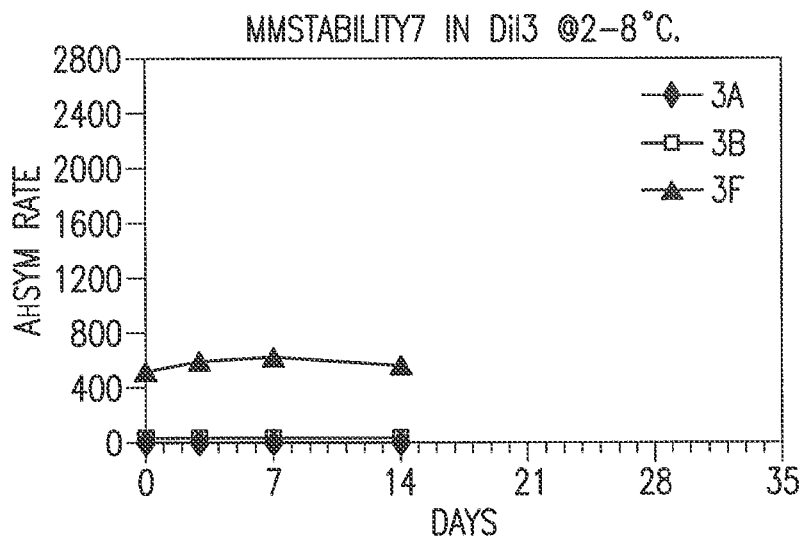
Figure 3N:
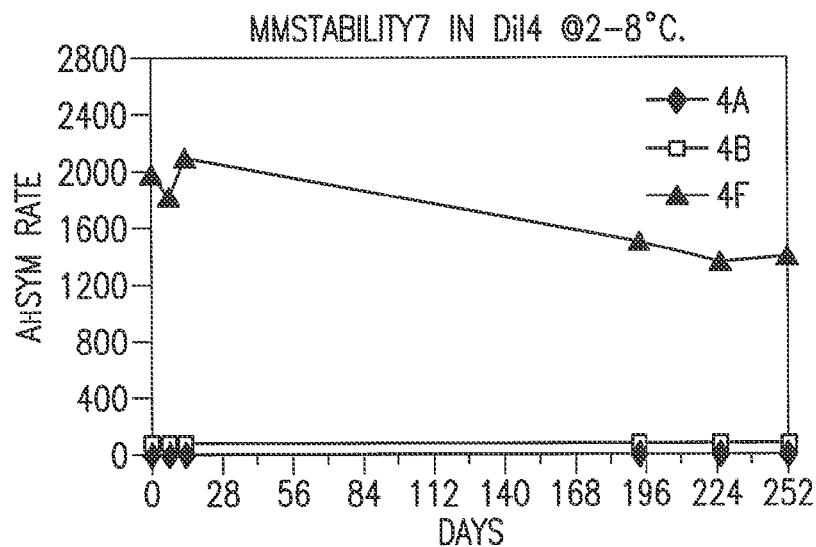
Figure 3O:
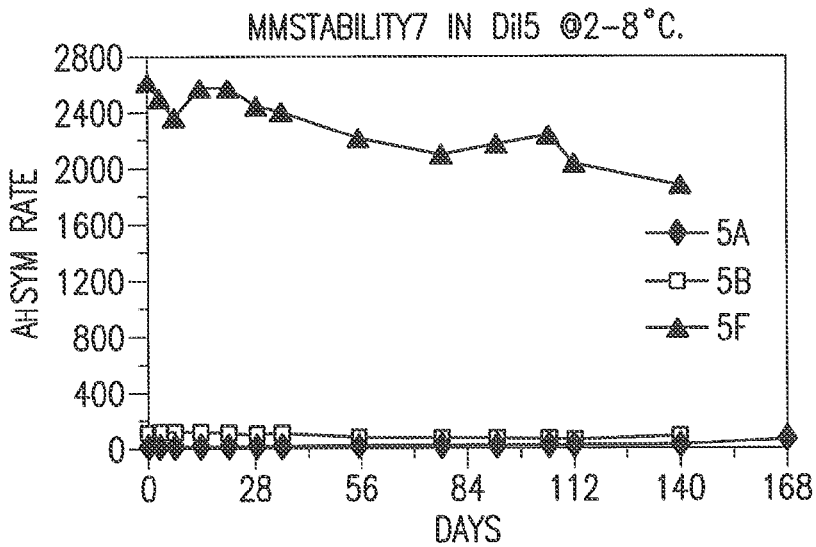
Figure 3P:
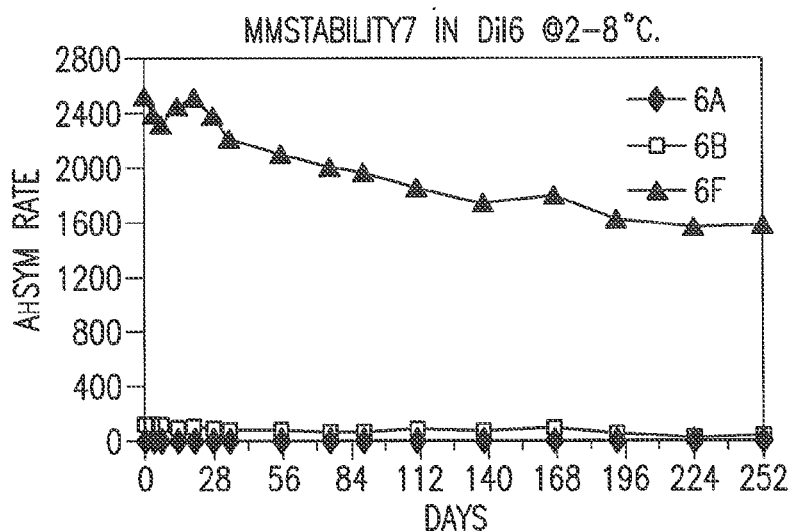
Figure 3Q:
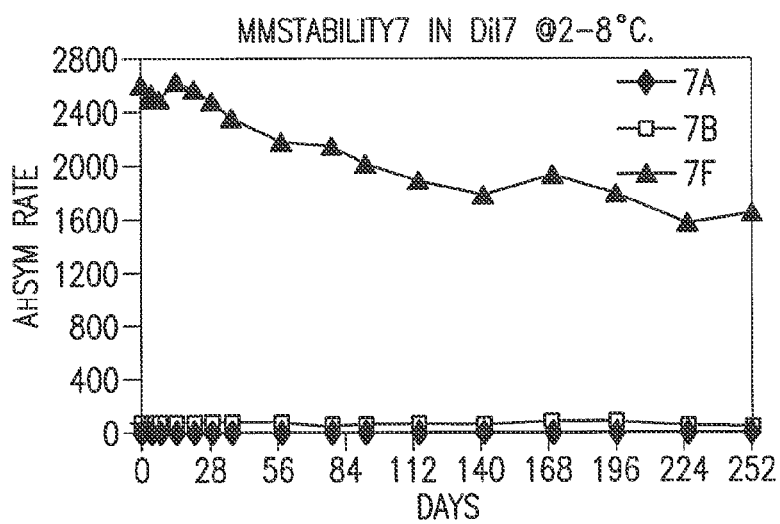
Figure 3R:
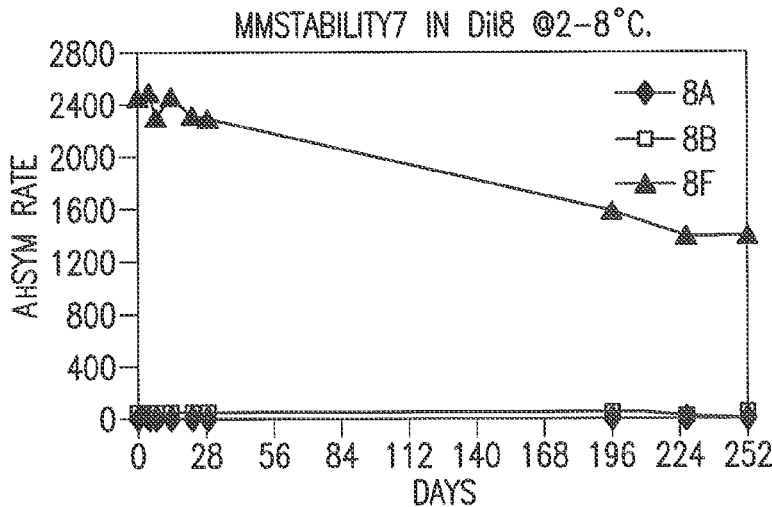
Figure 3S:
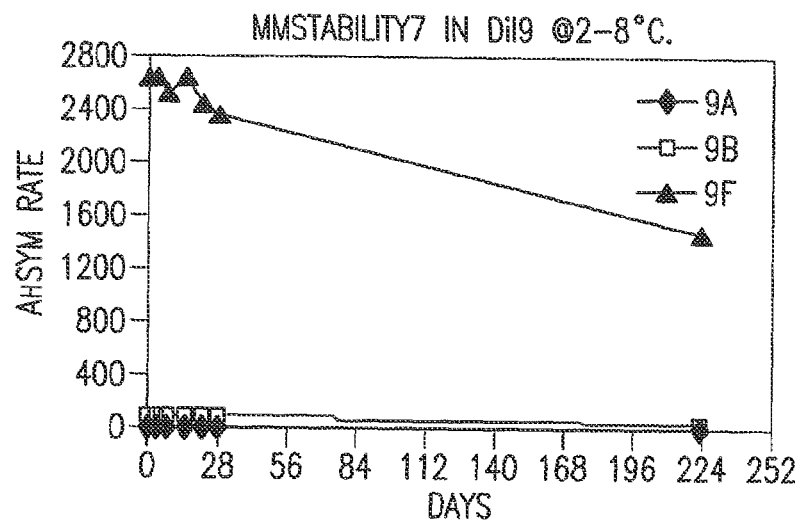
Figure 3T:
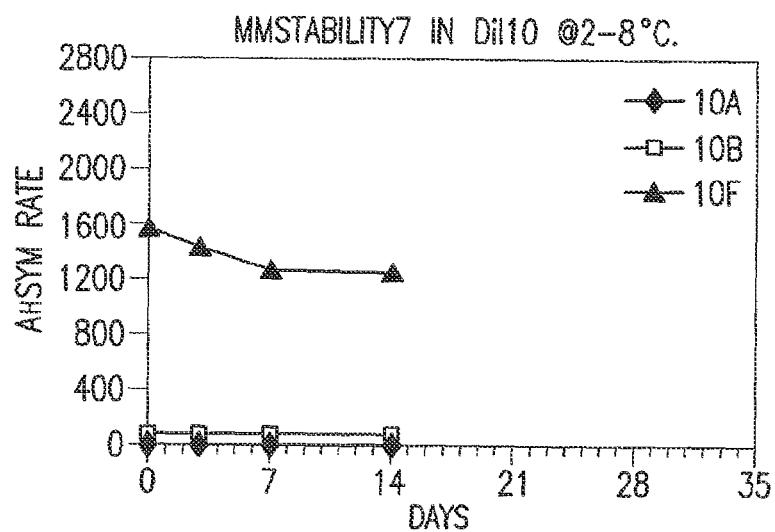

A BNP immunoassay was performed on an AxSYM® instrument as described in Example 1, the only change being that about 0.50 µg/mL of MAb BC203-conjugate in a conjugate buffer containing BSA, fish gelatin, Brij-35 and sodium azide was used. The assay was conducted twice for each calibrator. The results in Table 6 below and FIGS. 3A-3T show the mean of the two assays.

TABLE 6

| Calibrator stability at 37° C. or 2–8° C. for up to 252 days | | | | | | | | |
|---|---|---|---|---|---|---|---|---|
| 0 | 3 | 7 | 14 | 21 | 28 | 35 | 56 | 77 |

| | 0 | 3 | 7 | 14 | 21 | 28 | 35 | 56 | 77 |
|---|---|---|---|---|---|---|---|---|---|
| 37° C. | | | | | | | | | |
| 1A | 14.0 | 12.3 | 12.8 | 12.4 | 11.5 | 13.8 | 14.5 | 18.9 | 16.7 |
| 1B | 92.0 | 74.5 | 76.8 | 79.9 | 61.9 | 68.7 | 62.9 | 64.1 | 49.6 |
| 1F | 2413.7 | 2318.6 | 2056.3 | 2200.7 | 2004.3 | 1943.7 | 1803.7 | 1524.1 | 1499.2 |
| 5A | 11.5 | 12.7 | 14.4 | 17.9 | 11.4 | 16.0 | 15.2 | 17.6 | 17.2 |
| 5B | 96.0 | 81.5 | 77.5 | 76.6 | 61.8 | 70.6 | 67.0 | 61.6 | 58.1 |
| 5F | 2600.2 | 2406.2 | 2206.8 | 2212.0 | 2053.6 | 2078.9 | 2001.7 | 1784.2 | 1800.4 |
| 2A | 11.9 | 28.0 | 104.2 | 49.7 | | | | | |
| 2B | 91.7 | 68.2 | 95.4 | 58.5 | | | | | |
| 2F | 2477.4 | 2080.1 | 54.7 | 122.3 | | | | | |
| 4A | 11.3 | 35.6 | 27.7 | 55.8 | #N/A | #N/A | #N/A | #N/A | #N/A |
| 4B | 87.1 | 74.6 | 82.4 | 77.2 | #N/A | #N/A | #N/A | #N/A | #N/A |
| 4F | 1966.6 | 1769.2 | 1686.9 | 1901.0 | #N/A | #N/A | #N/A | #N/A | #N/A |
| 6A | 12.6 | 15.6 | 14.5 | 13.8 | 12.3 | 15.0 | 15.0 | 18.2 | 16.1 |
| 6B | 86.3 | 117.7 | 149.2 | 67.4 | 53.7 | 61.3 | 59.2 | 53.8 | 43.9 |
| 6F | 2548.6 | 2359.5 | 2187.1 | 2134.9 | 1997.1 | 1902.5 | 1857.1 | 1653.4 | 1553.2 |
| 7A | 11.4 | 11.2 | 17.3 | 12.5 | 11.6 | 14.8 | 13.5 | 17.3 | 18.4 |
| 7B | 99.0 | 71.3 | 70.5 | 68.4 | 56.5 | 55.6 | 50.5 | 46.8 | 40.5 |
| 7F | 2617.0 | 2308.4 | 2056.5 | 2120.1 | 1887.1 | 1780.3 | 1641.6 | 1326.0 | 1157.2 |
| 8A | 11.4 | 11.3 | 17.6 | 16.2 | 10.3 | 12.6 | #N/A | #N/A | #N/A |
| 8B | 92.1 | 65.9 | 60.5 | 55.9 | 44.0 | 43.7 | #N/A | #N/A | #N/A |
| 8F | 2474.9 | 2073.8 | 1882.4 | 1754.6 | 1572.6 | 1385.9 | #N/A | #N/A | #N/A |
| 9A | 12.5 | 10.4 | 13.9 | 14.3 | 13.3 | 13.8 | | | |
| 9B | 96.3 | 63.3 | 58.4 | 47.4 | 36.7 | 34.6 | | | |
| 9F | 2686.1 | 2175.9 | 1940.8 | 1643.5 | 1495.3 | 1158.3 | | | |
| 3A | 11.3 | 40.6 | 29.2 | 42.1 | | | | | |
| 3B | 25.7 | 24.9 | 20.7 | 30.7 | | | | | |
| 3F | 533.9 | 28.9 | 23.4 | 27.8 | | | | | |
| 10A | 15.1 | 12.4 | 15.4 | 13.9 | | | | | |
| 10B | 46.4 | 21.7 | 18.4 | 13.5 | | | | | |
| 10F | 1518.8 | 663.9 | 261.9 | 83.4 | | | | | |
| 2–8° C. | | | | | | | | | |
| 1A | 14.0 | 11.3 | 17.8 | 15.7 | 12.9 | 13.4 | 13.4 | 16.9 | 16.6 |
| 1B | 92.0 | 83.0 | 100.0 | 89.8 | 79.0 | 80.7 | 76.6 | 77.7 | 71.5 |
| 1F | 2413.7 | 2435.9 | 2330.2 | 2333.4 | 2429.0 | 2396.1 | 2269.7 | 2086.2 | 2068.8 |
| 5A | 11.5 | 10.6 | 13.9 | 12.2 | 11.4 | 14.0 | 13.1 | 18.5 | 19.2 |
| 5B | 96.0 | 86.3 | 88.4 | 92.5 | 79.1 | 88.5 | 81.5 | 75.6 | 70.0 |
| 5F | 2600.2 | 2480.7 | 2279.1 | 2548.5 | 2518.7 | 2415.9 | 2379.8 | 2210.6 | 2056.5 |
| 2A | 11.9 | 10.7 | 17.4 | 14.5 | #N/A | #N/A | #N/A | #N/A | #N/A |
| 2B | 91.7 | 80.6 | 87.0 | 78.0 | #N/A | #N/A | #N/A | #N/A | #N/A |
| 2F | 2477.4 | 2420.9 | 2341.0 | 2430.7 | #N/A | #N/A | #N/A | #N/A | #N/A |
| 4A | 11.3 | 10.2 | 14.6 | 15.0 | #N/A | #N/A | #N/A | #N/A | #N/A |
| 4B | 87.1 | 75.7 | 85.1 | 84.1 | #N/A | #N/A | #N/A | #N/A | #N/A |
| 4F | 1966.6 | 1926.3 | 1788.1 | 2098.1 | #N/A | #N/A | #N/A | #N/A | #N/A |
| 6A | 12.6 | 11.2 | 15.6 | 17.3 | 11.5 | 14.4 | 13.7 | 17.7 | 17.2 |
| 6B | 86.3 | 69.2 | 78.2 | 80.1 | 72.6 | 73.3 | 66.1 | 68.4 | 56.9 |
| 6F | 2548.6 | 2423.7 | 2307.8 | 2469.5 | 2529.9 | 2405.9 | 2236.6 | 2105.0 | 2032.9 |
| 7A | 11.4 | 10.7 | 13.1 | 12.1 | 11.8 | 16.5 | 15.6 | 18.2 | 16.3 |
| 7B | 99.0 | 84.7 | 89.3 | 89.6 | 87.0 | 87.6 | 83.8 | 82.9 | 73.0 |
| 7F | 2617.0 | 2511.7 | 2478.8 | 2634.6 | 2619.5 | 2504.0 | 2370.4 | 2184.6 | 2157.2 |
| 8A | 11.4 | 11.0 | 14.2 | 12.7 | 12.5 | 14.2 | #N/A | #N/A | #N/A |

TABLE 6-continued

Calibrator stability at 37° C. or 2–8° C. for up to 252 days

| | | | | | | | | |
|---|---|---|---|---|---|---|---|---|
| 8B | 92.1 | 84.7 | 84.7 | 86.7 | 73.4 | 75.8 | #N/A | #N/A | #N/A |
| 8F | 2474.9 | 2524.4 | 2286.1 | 2489.0 | 2354.1 | 2284.6 | #N/A | #N/A | #N/A |
| 9A | 12.5 | 10.3 | 14.0 | 13.0 | 12.5 | 15.1 | #N/A | #N/A | #N/A |
| 9B | 96.3 | 87.1 | 95.5 | 91.2 | 84.0 | 86.3 | #N/A | #N/A | #N/A |
| 9F | 2686.1 | 2682.7 | 2508.2 | 2662.3 | 2448.3 | 2372.0 | #N/A | #N/A | #N/A |
| 3A | 11.3 | 9.8 | 16.8 | 13.6 | | | | | |
| 3B | 25.7 | 28.6 | 33.9 | 29.6 | | | | | |
| 3F | 533.9 | 560.8 | 602.5 | 545.7 | | | | | |
| 10A | 15.1 | 11.9 | 17.5 | 16.6 | | | | | |
| 10B | 46.4 | 37.3 | 41.2 | 37.4 | | | | | |
| 10F | 1518.8 | 1407.2 | 1226.0 | 1238.1 | | | | | |

| | 91 | 106 | 112 | 140 | 168 | 193 | 224 | 252 |
|---|---|---|---|---|---|---|---|---|
| 37° C. | | | | | | | | |
| 1A | 19.0 | #N/A | 25.3 | 31.8 | 36.5 | | | |
| 1B | 50.6 | #N/A | 47.7 | 51.4 | 60.2 | | | |
| 1F | 1248.8 | #N/A | 1065.4 | 784.6 | 726.2 | | | |
| 5A | 17.5 | #N/A | 23.1 | 28.5 | 38.8 | | | |
| 5B | 55.4 | #N/A | 53.7 | 58.7 | 73.9 | | | |
| 5F | 1712.5 | #N/A | 1598.9 | 1375.2 | 1512.3 | | | |
| 2A | | | | | | | | |
| 2B | | | | | | | | |
| 2F | | | | | | | | |
| 4A | #N/A | #N/A | #N/A | #N/A | #N/A | 57.1 | | |
| 4B | #N/A | #N/A | #N/A | #N/A | #N/A | 53.2 | | |
| 4F | #N/A | #N/A | #N/A | #N/A | #N/A | 85.0 | | |
| 6A | 17.9 | #N/A | 26.4 | 28.6 | 44.3 | 31.3 | | |
| 6B | 45.9 | #N/A | 49.1 | 48.1 | 58.1 | 41.8 | | |
| 6F | 1517.0 | #N/A | 1266.3 | 1167.2 | 1061.1 | 885.9 | | |
| 7A | 17.2 | #N/A | 26.5 | 27.5 | 40.7 | 48.4 | | |
| 7B | 37.7 | #N/A | 44.9 | 42.6 | 62.8 | 48.4 | | |
| 7F | 1117.5 | #N/A | 901.0 | 759.3 | 744.5 | 619.0 | | |
| 8A | #N/A | #N/A | #N/A | #N/A | #N/A | 31.3 | | |
| 8B | #N/A | #N/A | #N/A | #N/A | #N/A | 37.8 | | |
| 8F | #N/A | #N/A | #N/A | #N/A | #N/A | 362.5 | | |
| 2–8° C. | | | | | | | | |
| 1A | 17.3 | 17.2 | 27.6 | #N/A | #N/A | depleted | | |
| 1B | 77.9 | 65.3 | 79.3 | 84.8 | #N/A | depleted | | |
| 1F | 1971.2 | 2024.2 | 1828.9 | 1799.3 | 1940.6 | depleted | | |
| 5A | 17.9 | 18.3 | 22.2 | 28.3 | 44.5 | depleted | | |
| 5B | 67.6 | 67.4 | 77.2 | 79.7 | #N/A | depleted | | |
| 5F | 2157.9 | 2217.0 | 1992.1 | 1872.0 | #N/A | depleted | | |
| 2A | #N/A | #N/A | #N/A | #N/A | #N/A | #N/A | 19.4 | 16.4 |
| 2B | #N/A | #N/A | #N/A | #N/A | #N/A | #N/A | 47.0 | 46.3 |
| 2F | #N/A | #N/A | #N/A | #N/A | #N/A | #N/A | 1586.4 | 1577.9 |
| 4A | #N/A | #N/A | #N/A | #N/A | #N/A | 28.0 | 16.8 | 17.8 |
| 4B | #N/A | #N/A | #N/A | #N/A | #N/A | 79.3 | 56.7 | 61.1 |
| 4F | #N/A | #N/A | #N/A | #N/A | #N/A | 1501.0 | 1380.2 | 1373.2 |
| 6A | 19.7 | #N/A | 29.0 | 29.8 | 42.4 | 31.5 | 21.9 | 19.5 |
| 6B | 60.1 | #N/A | 65.8 | 70.6 | 81.0 | 77.1 | 54.0 | 50.3 |
| 6F | 1966.8 | #N/A | 1871.1 | 1754.6 | 1816.0 | 1634.6 | 1608.2 | 1591.8 |
| 7A | 18.5 | #N/A | 27.7 | 31.1 | 42.1 | 32.3 | 20.5 | 18.4 |
| 7B | 70.5 | #N/A | 76.3 | 74.7 | 97.4 | 79.1 | 52.8 | 51.9 |
| 7F | 2016.7 | #N/A | 1898.1 | 1788.8 | 1940.9 | 1809.8 | 1579.4 | 1653.1 |
| 8A | #N/A | #N/A | #N/A | #N/A | #N/A | 31.4 | 18.0 | 16.5 |
| 8B | #N/A | #N/A | #N/A | #N/A | #N/A | 64.2 | 45.4 | 43.9 |
| 8F | #N/A | #N/A | #N/A | #N/A | #N/A | 1617.1 | 1430.4 | 1389.9 |
| 9A | #N/A | #N/A | #N/A | #N/A | #N/A | #N/A | 22.4 | 19.1 |
| 9B | #N/A | #N/A | #N/A | #N/A | #N/A | #N/A | 42.3 | 42.7 |
| 9F | #N/A | #N/A | #N/A | #N/A | #N/A | #N/A | 1478.5 | 1497.4 |

The data in Table 6 and FIGS. 3A-3T demonstrate that calibrators having a pH in the range of from about 4.0 to about 6.5 (calibrators in diluents 1, 4–8) exhibited less of a signal decrease than the calibrators in diluents 2–3 (at pH's of 3.91 and 3.47, note that #3 had low signal even at 0 time) and calibrators in diluents 9–10 (pH's 7.04 and 10.04) at 37° C. accelerated stability. At 2–8° C., little change in F Cal rates was observed through 14 days except for diluent #3 which had low signal even at 0 time and for diluent # 10 which decreased by 18.5%.

All abstracts, references, patents and published patent applications referred to herein are hereby incorporated by reference.

The present invention is illustrated by way of the foregoing description and examples. The foregoing description is intended as a non-limiting illustration, since many variations will become apparent to those skilled in the art in view thereof.

Changes can be made to the composition, operation and arrangement of the method of the present invention described herein without departing from the concept and scope of the invention.

What is claimed is:

1. A stable liquid calibrator or control for use in a ligand binding assay for measuring a level of a natriuretic peptide in a test sample, wherein said calibrator or control comprises at least one human synthetic natriuretic peptide, has a pH of from about 4.0 to about 6.5, and remains stable when stored at temperatures of from about 2 to about 8° C. for a period of about twelve (12) months.

2. The calibrator or control of claim 1, wherein said calibrator or control has a pH of from about 5.0 to about 6.0.

3. The calibrator or control of claim 1, wherein said human synthetic natriuretic peptide is selected from the group consisting of human synthetic atrial natriuretic peptide, human synthetic B-type natriuretic peptide, human synthetic C-type natriuretic peptide and human synthetic Dendroaspis natriuretic peptide.

4. The calibrator or control of claim 1, wherein said calibrator or control comprises at least one buffer, at least one acid, at least one base, or combinations thereof.

5. The calibrator or control of claim 4, wherein said buffer is selected from the group consisting of an acetate buffer, a citrate buffer, a phosphate buffer and combinations thereof.

6. The calibrator or control of claim 4, wherein said acid is selected from the group consisting of acetic acid, citric acid, diethylenetriaminepentaacetic acid, hydrochloric acid and combinations thereof.

7. The calibrator or control of claim 4, wherein the base is sodium hydroxide.

8. The calibrator or control of claim 4, wherein said calibrator or control comprises at least one diluent.

9. The calibrator or control of claim 8, wherein said diluent comprises at least one natriuretic stabilizing compound and at least one biocide.

10. The calibrator or control of claim 9, wherein said natriuretic stabilizing compound is a protein or a polymer.

11. The calibrator or control of claim 10, wherein the protein is selected from the group consisting of bovine serum albumin, bovine gamma globulin, and a non-fat dry milk.

12. The calibrator or control of claim 10, wherein the polymer is selected from the group consisting of polyethylene glycol, dextran, dextran sulfate and polyvinyl pyrrolidone.

13. The calibrator or control of claim 8, wherein the diluent further comprises at least one buffer, at least one acid, at least one base, or combinations thereof.

14. The calibrator or control of claim 13, wherein said buffer is selected from the group consisting of an acetate buffer, a citrate buffer, a phosphate buffer and combinations thereof.

15. The calibrator or control of claim 13, wherein said acid is selected from the group consisting of acetic acid, citric acid, diethylenetriaminepentaacetic acid, hydrochloric acid and combinations thereof.

16. The calibrator or control of claim 13, wherein the base is sodium hydroxide.

17. The calibrator or control of claim 1, wherein said calibrator or control can be used in an assay at ambient temperature or at a temperature of from about 30 to about 40° C.

18. A stable liquid calibrator or control for use in a ligand binding assay for measuring a level of a natriuretic peptide in a test sample, wherein said calibrator or control comprises:
at least one diluent; and
at least one human synthetic natriuretic peptide,
wherein said calibrator or control has a pH of from about 4.0 to about 6.0
wherein the calibrator or control remains stable when stored at temperatures of from about 2 to about 8° C. for a period of about twelve (12) months.

19. The calibrator or control of claim 18, wherein said calibrator or control has a pH of from about 5.0 to about 6.0.

20. The calibrator or control of claim 18, wherein the human synthetic natriuretic peptide is selected from the group consisting of human synthetic atrial natriuretic peptide, human synthetic B-type natriuretic peptide, human synthetic C-type natriuretic peptide and human synthetic Dendroaspis natriuretic peptide.

21. The calibrator or control of claim 18, wherein said calibrator or control further comprises at least one buffer, at least one acid, at least one base, or combinations thereof.

22. The calibrator or control of claim 21, wherein said buffer is selected from the group consisting of an acetate buffer, a citrate buffer, a phosphate buffer and combinations thereof.

23. The calibrator or control of claim 21, wherein said acid is selected from the group consisting of acetic acid, citric acid, diethylenetriaminepentaacetic acid, hydrochloric acid and combinations thereof.

24. The calibrator or control of claim 21, wherein the base is sodium hydroxide.

25. The calibrator or control of claim 18, wherein said diluent comprises at least one natriuretic stabilizing compound and at least one biocide.

26. The calibrator or control of claim 25, wherein said natriuretic stabilizing compound is a protein or a polymer.

27. The calibrator or control of claim 26, wherein the protein is selected from the group consisting of bovine serum albumin, a bovine gamma globulin, and a non-fat dry milk.

28. The calibrator or control of claim 25, wherein the polymer is selected from the group consisting of polyethylene glycol, dextran, dextran sulfate and polyvinyl pyrrolidone.

29. The calibrator or control of claim 25, wherein the diluent further comprises at least one buffer, at least one acid, at least one base, or combinations thereof.

30. The calibrator or control of claim 29, wherein said buffer is selected from the group consisting of an acetate buffer, a citrate buffer, a phosphate buffer and combinations thereof.

31. The calibrator or control of claim 29, wherein said acid is selected from the group consisting of acetic acid, citric acid, diethylenetriaminepentaacetic acid, hydrochloric acid and combinations thereof.

32. The calibrator or control of claim 29, wherein the base is sodium hydroxide.

33. The calibrator or control of claim 18, wherein said calibrator or control can be stored at a temperature of from about 2 to about 8° C.

34. The calibrator or control of claim 18, wherein said calibrator or control can be used in an assay at ambient temperature or at a temperature of from about 30 to about 40° C.

35. A stable liquid calibrator or control for use in a ligand binding assay for measuring a level of a natriuretic peptide in a test sample, wherein said calibrator or control comprises at least one human synthetic natriuretic peptide, has a pH of from about 4.0 to about 6.5 and is reusable.

* * * * *

UNITED STATES PATENT AND TRADEMARK OFFICE
CERTIFICATE OF CORRECTION

PATENT NO. : 7,445,933 B2 Page 1 of 1
APPLICATION NO. : 10/620475
DATED : November 4, 2008
INVENTOR(S) : Judith A. Friese et al.

It is certified that error appears in the above-identified patent and that said Letters Patent is hereby corrected as shown below:

Title Page, item (56); col. 2, lines 2-3 and 5-6;
First page, Other References: "myocardial infraction" to read as --myocardial infarction--

First Page, Other References: "Natriuretic Peptide as a Biomaker for" to read as --Natriuretic Peptide as a Biomarker for--

Column 2, lines 6-7, "elevated levels of BNP in human plasma has been" to read as --elevated levels of BNP in human plasma have been--

Column 12, line 38, "and 16 further examined" to read as --and 16 was further examined--

Signed and Sealed this

Fifteenth Day of June, 2010

David J. Kappos
*Director of the United States Patent and Trademark Office*